US007628985B2

(12) United States Patent
Shan et al.

(10) Patent No.: US 7,628,985 B2
(45) Date of Patent: *Dec. 8, 2009

(54) THERAPEUTIC ENZYME FORMULATIONS AND USES THEREOF IN CELIAC SPRUE AND/OR DERMATITIS HERPETOFORMIS

(75) Inventors: Lu Shan, Houston, TX (US); Michael Thomas Bethune, Stanford, CA (US); Chaitan Khosla, Palo Alto, CA (US); Jonathan David Gass, Mountain View, CA (US)

(73) Assignees: The Board of Regents of the Leland Stanford Junior University, Palo Alto, CA (US); Alvine Pharmaceuticals, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/587,217

(22) PCT Filed: Feb. 23, 2005

(86) PCT No.: PCT/US2005/006129

§ 371 (c)(1),
(2), (4) Date: Sep. 4, 2007

(87) PCT Pub. No.: WO2005/107786

PCT Pub. Date: Nov. 17, 2005

(65) Prior Publication Data

US 2008/0193436 A1 Aug. 14, 2008

Related U.S. Application Data

(63) Continuation-in-part of application No. 10/969,314, filed on Oct. 19, 2004, now Pat. No. 7,320,788.

(60) Provisional application No. 60/565,668, filed on Apr. 26, 2004.

(51) Int. Cl.
*A61K 38/48* (2006.01)
*A61K 9/00* (2006.01)
*A61K 31/785* (2006.01)
*A61K 38/02* (2006.01)

(52) U.S. Cl. ............... 424/94.63; 424/400; 424/78.16; 514/2

(58) Field of Classification Search ............. None
See application file for complete search history.

(56) References Cited

U.S. PATENT DOCUMENTS

| 4,203,967 | A | 5/1980 | Gallo-Torres |
| 4,912,120 | A | 3/1990 | Castelhano et al. |
| 4,929,630 | A | 5/1990 | Castelhano et al. |
| 5,817,523 | A | 10/1998 | Picarelli |
| 5,834,428 | A | 11/1998 | Drucker |
| 6,197,356 | B1 | 3/2001 | Girsh |
| 6,319,726 | B1 | 11/2001 | Schuppan et al. |
| 6,410,550 | B1 | 6/2002 | Coe et al. |
| 7,144,569 | B1 | 12/2006 | Anderson et al. |
| 2001/0007690 | A1* | 7/2001 | Girsh .................... 426/442 |
| 2001/0036639 | A1 | 11/2001 | Fine |
| 2002/0039599 | A1 | 4/2002 | Lin et al. |
| 2002/0076834 | A1 | 6/2002 | Detlef et al. |
| 2003/0215438 | A1 | 11/2003 | Hausch et al. |
| 2003/0224476 | A1 | 12/2003 | Chou |
| 2004/0167069 | A1 | 8/2004 | Khosla et al. |
| 2004/0241664 | A1* | 12/2004 | Dekker et al. ............ 435/6 |
| 2005/0090653 | A1 | 4/2005 | Klaveness et al. |
| 2005/0244823 | A1 | 11/2005 | Drijfhout et al. |
| 2006/0178299 | A1 | 8/2006 | Anderson et al. |

FOREIGN PATENT DOCUMENTS

| EP | 0237082 | 9/1987 |
| EP | 0905518 A1 | 3/1999 |
| WO | WO94/26774 A1 | 11/1994 |
| WO | WO01/25793 A2 | 4/2001 |
| WO | WO03/068170 A2 | 8/2003 |

OTHER PUBLICATIONS

Shan et al. (2004) Biochem J. 383: 311-318.*
Arentz-Hansen et al. "Celiac Lesion T Cells Recognizes Epitopes that Cluster in Regions of Gliadins Rich in Proline Residues" Gastroenterology, 2002, pp. 803-809, vol. 123, No. 3.
Bethune, et al. "Heterologous expression, purification, refolding, and structural-functional characterization of EP-B2, a self-activating barley cysteine endoprotease," Chemistry & Biology, 2006, pp. 637-647, vol. 13.
Castelhano et al., "Synthesis, Chemistry, and Absolute Configuratin of Novel Transglutaminiase Inhibitors Containing a 3-Halo-4,5-dihydroisoxazole" Bioorg. Chem., 1988, pp. 335-340, vol. 16.
Choi et al. "Chemistry and Biology of Dihydroisoxazole Derivatives: Selectives Inhibitors of Human Transglutaminase 2" Chem. & Biol., 2005, pp. 469-475, vol. 12.
de Ritis G. et al. "In Vitro (organ culture) Studies of the Toxicity of Specific A-Gliadin Peptides in celiac Disease" Gastroenbterology, 1988, pp. 41-49, vol. 94.
Freund, K. et al. "Transglutaminase inhibition by 2-[(2-Oxopropyl)thio]imidazolium derivatives: mechanism of factor XIIIa inactivation" Biochemistry, 1994, pp. 10109-10119, vol. 33.
Greenberg, C. et al. "Transglutaminases: multifunctional cross-linking enzymes that stabilize tissues" FASEB J., 1991, pp. 3071-3077, vol. 5.
Hartmann, G. et al. "Rapid degradation of gliadin peptides toxic for coeliac disease patients by proteases from germinating cereals" Journal of Cereal Science, Nov. 2006, pp. 368-371, vol. 44.

(Continued)

*Primary Examiner*—Lisa J Hobbs
(74) *Attorney, Agent, or Firm*—Bozicevic, Field & Francis LLP; Pamela J. Sherwood

(57) ABSTRACT

Pharmaceutical formulations of glutenase enzymes are provided. The enzymes find particular use in the treatment of a Celiac or dermatitis herpetiformis patient.

17 Claims, 11 Drawing Sheets

OTHER PUBLICATIONS

Hausch et al. "Design, synthesis, and evaluation of gluten peptide analogs as selective inhibitors of human tissue transglutaminase" Chem Biol., Mar. 2003, pp. 225-231, vol. 10, Issue 3.

Hitomi, K. et al. "GTP, an inhibitor of transglutaminases, is hydrolyzed by tissue-type transglutaminase (TGase 2) but not by epidermal-type transglutaminase (TGase 3)," Biosci. Biotechnol. Biochem., 2000, pp. 657-659, vol. 64, Issue 3.

Kao Castle Pty Ltd Sequence Analysis PCTRIS03104743.

Karpuj et al. "Prolonged survival and decreased abnormal movements in transgenic model of Huntington disease, with administration of the transglutaminase inhibitor cystamine" Nature Med., Feb. 2002, pp. 143-149, vol. 8, Issue 2.

Keillor, J. "Tissue Transglutaminase Inhibition" Chem. & Biol., 2005, pp. 410-412, vol. 12.

Kim et al. "Transglutaminases in disease" Neurochem. Int., 2002, pp. 85-103, vol. 40.

Lorand et al. "Novel inhibitors against the transglutaminase-catalysed crosslinking of lens proteins" Exp Eye Res., May 1998, pp. 531-536, vol. 66.

Martinet et al. "In vivo transglutaminase type 1 expression in normal lung, preinvasive bronchial lesions, and lung cancer" Am J Respir Cell Mol Biol., Apr. 2003, pp. 428-435, vol. 28, Issue 4.

Piper et al., "High selectivity of human tissue transglutaminase for immunoactive gliadin peptides: implications for celiac spure", Biochemistry, Jan. 8, 2002, pp. 386-393, vol. 41, Issue 1.

Piper, J., et al., "Effect of prolyl endopeptidase on digestive-resistant gliadin peptides in vivo," The Journal of Pharmacology and Experimental Therapeutics, 2004, pp. 213-219, vol. 311, Issue 1.

Sárdy, M. et al. "Epidermal transglutaminase (TGase 3) is the autoantigen of dermatitis herpetiformis" J. Exp. Med., 2002, pp. 747-757, vol. 195, Issue 6.

Shan, L. et al. "Structural Basis for Gluten Intolerance in Celiac Sprue" Science 2002, pp. 2275-2279, vol. 297.

Shan, L. et al. "Comparative biochemical analysis of three bacterial prolyl endopeptidases: implications of coeliac sprue," Biochem J, 2004, pp. 311-318, vol. 383.

Sjostrom et al. "Identification of a Gliadin T-Cell Epitope in Coeliac Disease: General Importance of Gliadin Deamidation for Intestinal T-Cell Recognition" Scandinavian Journal of Immunology, Aug. 1998 , pp. 111-115(5), vol. 48, No. 2.

Stepniak, D. et al. "Highly efficient gluten degradation with a newly identified prolyl endoprotease: implications for celiac disease,"Am J Physiol Gastrointest Liver Physiol, 2006, pp. G621-G629, vol. 291.

Vader et al. "The Gluten Response in Children with Celiac Sprue Disease is Directed Toward Multiple Gliadin and Glutenin Peptides" Gastroenterology, 2002, pp. 1729-1737, vol. 122.

Vader et al. "The HLa-DQ2 Gene Dose Effect in Celiac Disease is Doirectly Related to the Magnitude and Breadth of Gluten-Specific T Cell Responses" PNAS, Oct. 14, 2003, pp. 12390-12395, vol. 123, No. 3.

Zhang et al. "Identification of differentially expressed proteins in human glioblastoma cell lines and tumors" Glia., Apr. 15, 2003, pp. 194-208, vol. 42, Issue 2.

Ahnen et al., "Intestinal aminooligopeptidase. In vivo synthesis on intracellular membranes of rat jejunum," J Biol. Chem., 1982, 257(20):12129-12135.

Arentz-Hansen et al., "Intestinal T cell response to alpha-gliadin in adult celiac disease is focused on a single deamidated glutamine targeted by tissue transglutaminase," J Exp. Med., 2000, 191(4):603-612.

Bordusa et al., "The specificity of prolyl endopeptidase from *Flavobacterium meningoseptum*: mapping the S' subsites by positional scanning via acyl transfer," Bioorg. Med. Chem., 1998, 6(10):1775-1780.

Colot, Genet. Eng. (NY), "The genes encoding wheat storage proteins: towards a molecular understanding of bread-making quality and its genetic manipulation," 1990, 12:225-241.

Database Derwent, Acc-No. 1996-329479. HIa-Binding Oligopeptide And An Immuno: Regulator Contgit—Used In The Treatment Of Auto: Immune Disease, 1999.

Frazer et al., "Gluten-induced enteropathy: the effect of partially digested gluten," Lancet, 1959, 2(7097):252-255.

Lahteenoja et al., "Local challenge on oral mucosa with an alpha-gliadin related synthetic peptide in patients with celiac disease," Am J Gastroenterol., 2000, 95(10):2880-2887.

Lion. *Flavobacterium meningosepticum*. Genbank Accession #/EMBL #: D10980. Aug. 1, 1992. http://www. infobiogen.fr/srs71bin/cgi-bin/wgetz?-id+4jqa61Mc9PO+[uniprot-ID:PPCE_FLAME]+-e.

Messer et al., "Studies on the mechanism of destruction of the toxic action of wheat gluten in celiac disease by crude papain," Gut, 1964, 5:295-303.

Messer et al., "Oral papain in gluten intolerance," Lancet, 1976, 2(7993):1022.

Moodie, Peter, "Traditional Baking Enzymes-Proteases," Enzyme Development Corporation, 2001, pp. 1-10.

Online-Medical Dictionary. "Amino acid". http://cancerweb.ncl.ac.uk/cgi-bin/omd?query=amino+acid. Nov. 13, 1997.

Schuppan, "Current concepts of celiac disease pathogenesis," Gastroenterology, 119(1):234-242, Dec. 2000.

Wieser, "The precipitating factor in coeliac disease," Baillieres Clin. Gastroenterol., 9(2):191-207, Jun. 1995.

Wieser, "Relation between gliadin structure and coeliac toxicity," Acta Paediatr. Suppl., 1996, 412:3-9.

Yoshimoto et al., "Prolyl endopeptidase from *Flavobacterium meningosepticum*: cloning and sequencing of the enzyme gene," J Biochem., 1991, 110(6):873-878.

Cornell; et al., "In vitro mucosal digestion of synthetic gliadin-derived peptides in celiac disease", Journal of Protein Chemistry (1995) 14(5):335-339.

Smith; et al., "Abnormal expression of dipeptidylpeptidase IV activity in enterocyte brush-border membranes of children suffering from coeliac disease", Experimental Physiology (1990), 75(4):613-616.

Wruble; et al., "Enteric Coatings. I. A Laboratory Method for the Study and Control of Enteric Coatings", Journal of the American Pharmaceutical Association (1935), XXIV(7):570-574.

* cited by examiner

| | |
|---|---|
| LQLQPFPQPQLPYPQPQLPYPQPQLPYPQPQPF | MW (FM) |
| QPQPF | 616.3 |
| QPQLP    QPQLP    QPQLP | 582.2 |
| YPQPQLPYP | 1102.5 |
| YPQPQLPYP | |
| QPQLPYP | 842.4 |
| QPQLPYPQPQPF | 1439.7 |
| LQLQPFP | 842.3 |
| LQLQPFPQPQLP | 1405.6 |
| LQLQPFPQPQLPYP | 1665.7 |
| LQLQPFPQPQLPYPQPQLP | 2231.0 |

| | |
|---|---|
| LQLQPFPQPQLPYPQPQLPYPQPQLPYPQPQPF | MW (MX) |
| YPQPQPF | 876.4 |
| QPQPF | 616.3 |
| QPQLP    QPQLP    QPQLP | 582.2 |
| LQLQP | 598.2 |
| FPQP | 488.2 |
| YPQP    YPQP    YPQP | 504.2 |

SEQUENCE LISTING

<160> NUMBER OF SEQ ID NOS: 47

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
1               5                   10

<210> SEQ ID NO 2
<211> LENGTH: 26
<212> TYPE: DNA
<213> ORGANISM: Artificial Sequence
<220> FEATURE:
<223> OTHER INFORMATION: synthetic primer

<400> SEQUENCE: 2
gataaaaacg gaaagcttgt aagggc                                          26

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
1               5                   10

<210> SEQ ID NO 4
<211> LENGTH: 40
<212> TYPE: DNA
<213> ORGANISM: Artificial Sequence
<220> FEATURE:
<223> OTHER INFORMATION: synthetic primer

<400> SEQUENCE: 4
cccttaattt tcaaatttta gctcgagttt atgatttata                           40

<210> SEQ ID NO 5
<211> LENGTH: 29
<212> TYPE: DNA
<213> ORGANISM: Artificial Sequence
<220> FEATURE:
<223> OTHER INFORMATION: synthetic primer

<400> SEQUENCE: 5
aggatatcca tatgaagaac cgcttgtgg                                       29

<210> SEQ ID NO 6
<211> LENGTH: 25
<212> TYPE: DNA
<213> ORGANISM: Artificial Sequence
<220> FEATURE:
<223> OTHER INFORMATION: synthetic primer

<400> SEQUENCE: 6
gacaacctcg aatccgtcgg cattg                                           25

<210> SEQ ID NO 7
<211> LENGTH: 25
<212> TYPE: DNA
<213> ORGANISM: Artificial Sequence

```
<220> FEATURE:
<223> OTHER INFORMATION: synthetic primer

<400> SEQUENCE: 7
caatgccgac ggattcgagg ttgtc                                        25

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
cgcggggacc tcgagtagaa actg                                         24

<210> SEQ ID NO 9
<211> LENGTH: 26
<212> TYPE: DNA
<213> ORGANISM: Artificial Sequence
<220> FEATURE:
<223> OTHER INFORMATION: synthetic primer

<400> SEQUENCE: 9
ctccccatat gtcctacccg gcgacc                                       26

<210> SEQ ID NO 10
<211> LENGTH: 32
<212> TYPE: DNA
<213> ORGANISM: Artificial Sequence
<220> FEATURE:
<223> OTHER INFORMATION: synthetic primer

<400> SEQUENCE: 10
gtggcggcgc agggccgcaa gcttcccaag cg                                32

<210> SEQ ID NO 11
<211> LENGTH: 13
<212> TYPE: PRT
<213> ORGANISM: Triticum aestivum

<400> SEQUENCE: 11

Pro Gln Pro Gln Leu Pro Tyr Pro Gln Pro Gln Leu Pro
1               5                   10

<210> SEQ ID NO 12
<211> LENGTH: 33
<212> TYPE: PRT
<213> ORGANISM: Triticum aestivum

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 13
<211> LENGTH: 10
<212> TYPE: PRT
<213> ORGANISM: Triticum aestivum

<400> SEQUENCE: 13

Gln Pro Gln Gln Ser Phe Pro Gln Gln Gln
```

1           5                   10

<210> SEQ ID NO 14
<211> LENGTH: 12
<212> TYPE: PRT
<213> ORGANISM: Triticum aestivum

<400> SEQUENCE: 14

Gln Leu Gln Pro Phe Pro Gln Pro Glu Leu Pro Tyr
1               5                   10

<210> SEQ ID NO 15
<211> LENGTH: 14
<212> TYPE: PRT
<213> ORGANISM: Triticum aestivum

<400> SEQUENCE: 15

Pro Gln Pro Glu Leu Pro Tyr Pro Gln Pro Glu Leu Pro Tyr
1               5                   10

<210> SEQ ID NO 16
<211> LENGTH: 10
<212> TYPE: PRT
<213> ORGANISM: Triticum aestivum

<400> SEQUENCE: 16

Gln Pro Gln Gln Ser Phe Pro Glu Gln Gln
1               5                   10

<210> SEQ ID NO 17
<211> LENGTH: 13
<212> TYPE: PRT
<213> ORGANISM: Triticum aestivum

<400> SEQUENCE: 17

Pro Gln Pro Glu Leu Pro Tyr Pro Gln Pro Gln Leu Pro
1               5                   10

<210> SEQ ID NO 18
<211> LENGTH: 14
<212> TYPE: PRT
<213> ORGANISM: Triticum aestivum

<400> SEQUENCE: 18

Pro Gln Pro Glu Leu Pro Tyr Pro Gln Pro Gln Pro Leu Pro
1               5                   10

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 9
<212> TYPE: PRT
<213> ORGANISM: Triticum aestivum

<400> SEQUENCE: 30

Ile Gln Pro Gln Gln Pro Ala Gln Leu
1               5

<210> SEQ ID NO 31
<211> LENGTH: 9
<212> TYPE: PRT
<213> ORGANISM: Triticum aestivum

<400> SEQUENCE: 31

Gln Gln Pro Gln Gln Pro Tyr Pro Gln
1               5

<210> SEQ ID NO 32

```
<211> LENGTH: 9
<212> TYPE: PRT
<213> ORGANISM: Triticum aestivum

<400> SEQUENCE: 32

Ser Gln Pro Gln Gln Gln Phe Pro Gln
1               5

<210> SEQ ID NO 33
<211> LENGTH: 9
<212> TYPE: PRT
<213> ORGANISM: Triticum aestivum

<400> SEQUENCE: 33

Gln Gln Pro Phe Pro Gln Gln Pro Gln
1               5

<210> SEQ ID NO 34
<211> LENGTH: 9
<212> TYPE: PRT
<213> ORGANISM: Triticum aestivum

<400> SEQUENCE: 34

Pro Phe Ser Gln Gln Gln Gln Pro Val
1               5

<210> SEQ ID NO 35
<211> LENGTH: 26
<212> TYPE: PRT
<213> ORGANISM: Triticum aestivum

<400> SEQUENCE: 35

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 36
<211> LENGTH: 7
<212> TYPE: PRT
<213> ORGANISM: Triticum aestivum
<220> FEATURE:
<221> NAME/KEY: VARIANT
<222> LOCATION: (1)...(1)
<223> OTHER INFORMATION: Glutamine with an O-AMINO- BENZOIC ACID moiety
<220> FEATURE:
<221> NAME/KEY: VARIANT
<222> LOCATION: (6)...(6)
<223> OTHER INFORMATION: Xaa = Tyrosine with a NO2 attached

<400> SEQUENCE: 36

Gln Pro Gln Gln Pro Xaa Asp
1               5

<210> SEQ ID NO 37
<211> LENGTH: 9
<212> TYPE: PRT
<213> ORGANISM: Triticum aestivum

<400> SEQUENCE: 37

Pro Phe Pro Gln Pro Gln Leu Pro Tyr
1               5

<210> SEQ ID NO 38
<211> LENGTH: 9
<212> TYPE: PRT
```

```
<213> ORGANISM: Triticum aestivum

<400> SEQUENCE: 38

Pro Gln Pro Gln Leu Pro Tyr Pro Gln
1               5

<210> SEQ ID NO 39
<211> LENGTH: 9
<212> TYPE: PRT
<213> ORGANISM: Triticum aestivum

<400> SEQUENCE: 39

Pro Gln Gln Ser Phe Pro Gln Gln Gln
1               5

<210> SEQ ID NO 40
<211> LENGTH: 6
<212> TYPE: PRT
<213> ORGANISM: Triticum aestivum
<220> FEATURE:
<221> NAME/KEY: VARIANT
<222> LOCATION: (1)...(1)
<223> OTHER INFORMATION: Glutamine with an O-AMINO- BENZOIC ACID moiety
<220> FEATURE:
<221> NAME/KEY: VARIANT
<222> LOCATION: (4)...(4)
<223> OTHER INFORMATION: Xaa = Tyrosine with a NO2 attached

<400> SEQUENCE: 40

Gln Leu Pro Xaa Pro Gln
1               5

<210> SEQ ID NO 41
<211> LENGTH: 7
<212> TYPE: PRT
<213> ORGANISM: Triticum aestivum
<220> FEATURE:
<221> NAME/KEY: VARIANT
<222> LOCATION: (1)...(1)
<223> OTHER INFORMATION: Proline with an O-AMINO- BENZOIC ACID moiety
<220> FEATURE:
<221> NAME/KEY: VARIANT
<222> LOCATION: (7)...(7)
<223> OTHER INFORMATION: Xaa = Tyrosine with a NO2 attached

<400> SEQUENCE: 41

Pro Tyr Pro Gln Pro Gln Xaa
1               5

<210> SEQ ID NO 42
<211> LENGTH: 13
<212> TYPE: PRT
<213> ORGANISM: Triticum aestivum
<220> FEATURE:
<221> NAME/KEY: VARIANT
<222> LOCATION: (4)...(4)
<223> OTHER INFORMATION: Lysine with an O-AMINO- BENZOIC ACID moiety
<220> FEATURE:
<221> NAME/KEY: VARIANT
<222> LOCATION: (7)...(7)
<223> OTHER INFORMATION: Xaa - Tyrosine with an NO2 attached

<400> SEQUENCE: 42

Pro Gln Pro Lys Leu Pro Xaa Pro Gln Pro Gln Leu Pro
1               5                   10

<210> SEQ ID NO 43
<211> LENGTH: 13
<212> TYPE: PRT
```

```
<213> ORGANISM: Triticum aestivum
<220> FEATURE:
<221> NAME/KEY: VARIANT
<222> LOCATION: (7)...(7)
<223> OTHER INFORMATION: Xaa = Tyrosine with a NO2 attached
<220> FEATURE:
<221> NAME/KEY: VARIANT
<222> LOCATION: (11)...(11)
<223> OTHER INFORMATION: Lysine with an O-AMINO- BENZOIC ACID moiety

<400> SEQUENCE: 43

Pro Gln Pro Gln Leu Pro Xaa Pro Gln Pro Lys Leu Pro
1               5                   10

<210> SEQ ID NO 44
<211> LENGTH: 34
<212> TYPE: DNA
<213> ORGANISM: Artificial Sequence
<220> FEATURE:
<223> OTHER INFORMATION: synthetic primer

<400> SEQUENCE: 44
aaccaatcat atgaagtaca acaaactttc tgtg                              34

<210> SEQ ID NO 45
<211> LENGTH: 26
<212> TYPE: DNA
<213> ORGANISM: Artificial Sequence
<220> FEATURE:
<223> OTHER INFORMATION: synthetic primer

<400> SEQUENCE: 45
gcccttacaa gctttccgtt tttatc                                       26

<210> SEQ ID NO 46
<211> LENGTH: 17
<212> TYPE: PRT
<213> ORGANISM: Artificial Sequence
<220> FEATURE:
<223> OTHER INFORMATION: synthetic peptide

<400> SEQUENCE: 46

Tyr Gln Glu Pro Val Leu Gly Pro Val Arg Gly Pro Phe Pro Ile Ile
1               5                   10                  15

Val

<210> SEQ ID NO 47
<211> LENGTH: 9
<212> TYPE: PRT
<213> ORGANISM: Artificial Sequence
<220> FEATURE:
<223> OTHER INFORMATION: synthetic peptide

<400> SEQUENCE: 47

Arg Pro Lys His Pro Ile Lys His Gln
1               5
```

THERAPEUTIC ENZYME FORMULATIONS AND USES THEREOF IN CELIAC SPRUE AND/OR DERMATITIS HERPETOFORMIS

FEDERALLY-SPONSORED RESEARCH OR DEVELOPMENT

This invention was made with Government support under contract DK063158 awarded by the National Institutes of Health. The Government has certain rights in this invention.

BACKGROUND OF THE INVENTION

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients supports a theory of an immunological nature of the disease. Antibodies to tissue transglutaminase (tTG) and gliadin appear in almost 100% of the patients with active Celiac Sprue, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villus atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue, improved methods of treating or ameliorating the effects of the disease are needed. The present invention addresses such needs.

SUMMARY OF THE INVENTION

The present invention provides glutenase enzymes and enzyme formulations useful in the treatment of Celiac Sprue and/or dermatitis herpetiformis. The enzymes decrease the levels of toxic gluten oligopeptides in foodstuffs, either prior to or after ingestion by a patient. Enzymes of interest include prolyl endopeptidases (PEP), e.g. the *Myxococcus xanthus* PEP; and endoprotease, e.g. *Hordeum vulgare* subsp. *vulgare* EPB2, biologically active fragments or derivatives thereof. Certain gluten oligopeptides known to be resistant to cleavage by gastric and pancreatic enzymes are digested by such enzymes, thereby preventing or relieving their toxic effects in Celiac Sprue or dermatitis herpetiformis patients.

In one embodiment, the invention provides purified *Myxococcus xanthus* PEP, biologically active fragments or derivatives thereof; and pharmaceutical formulations thereof. The enzyme can be expressed in a heterologous host cell, e.g. a heterologous bacteria, and purified by affinity chromatography. It is found that the enzyme can be purified, lyophilized, and formulated into unit does, such as tablets, enteric coated capsules, etc., while substantially retaining biological activity. Formulations of interest include formulations in which the enzyme is contained within an enteric coating that allows delivery of the active agent to the intestine and formulations in which the active agents are stabilized to resist digestion in acidic stomach conditions. The formulation may comprise one or more enzymes or a mixture or "cocktail" of agents having different activities.

These and other aspects and embodiments of the invention are described in more detail below.

Figure 4A:
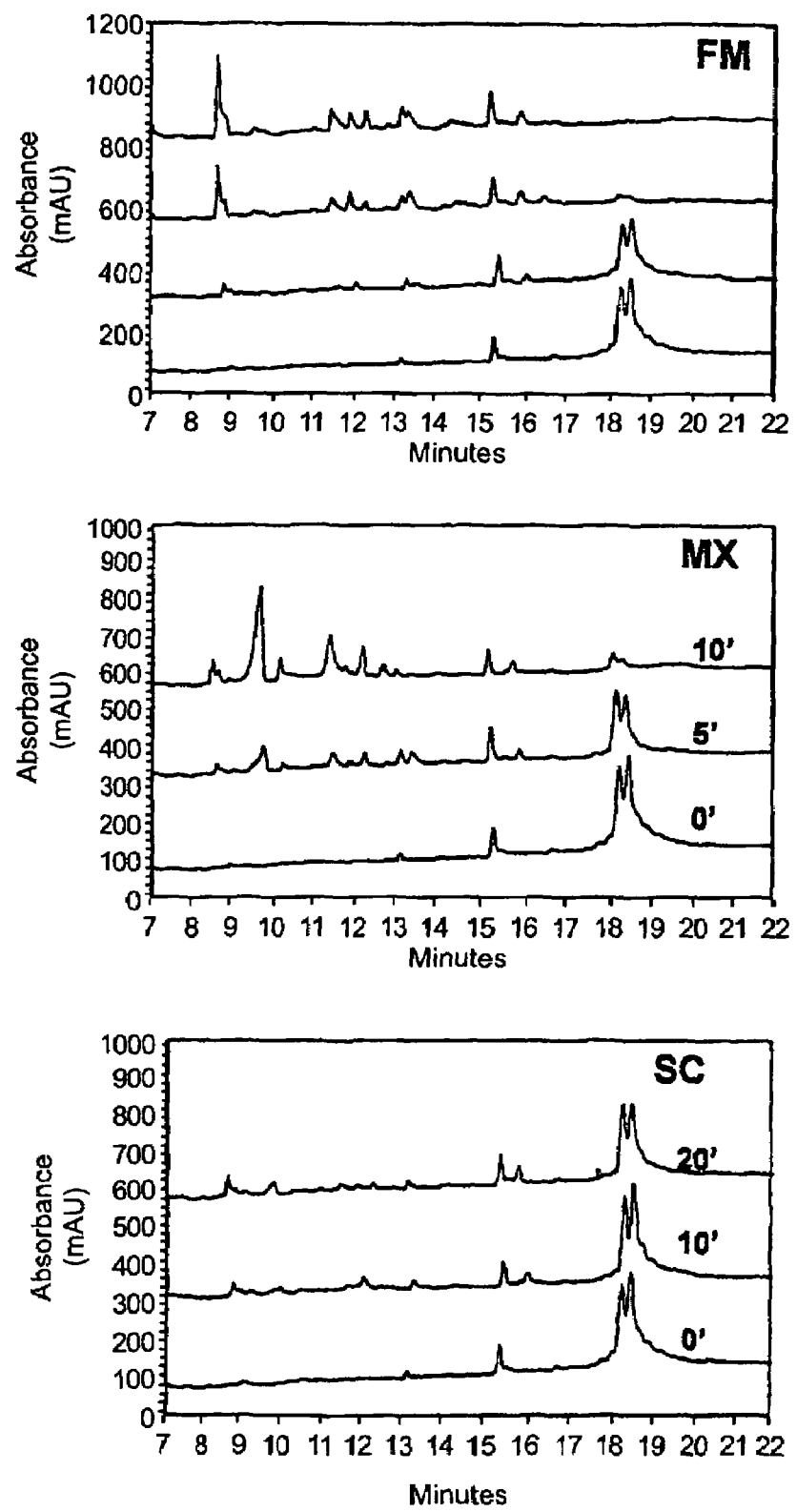
Figure 4B:
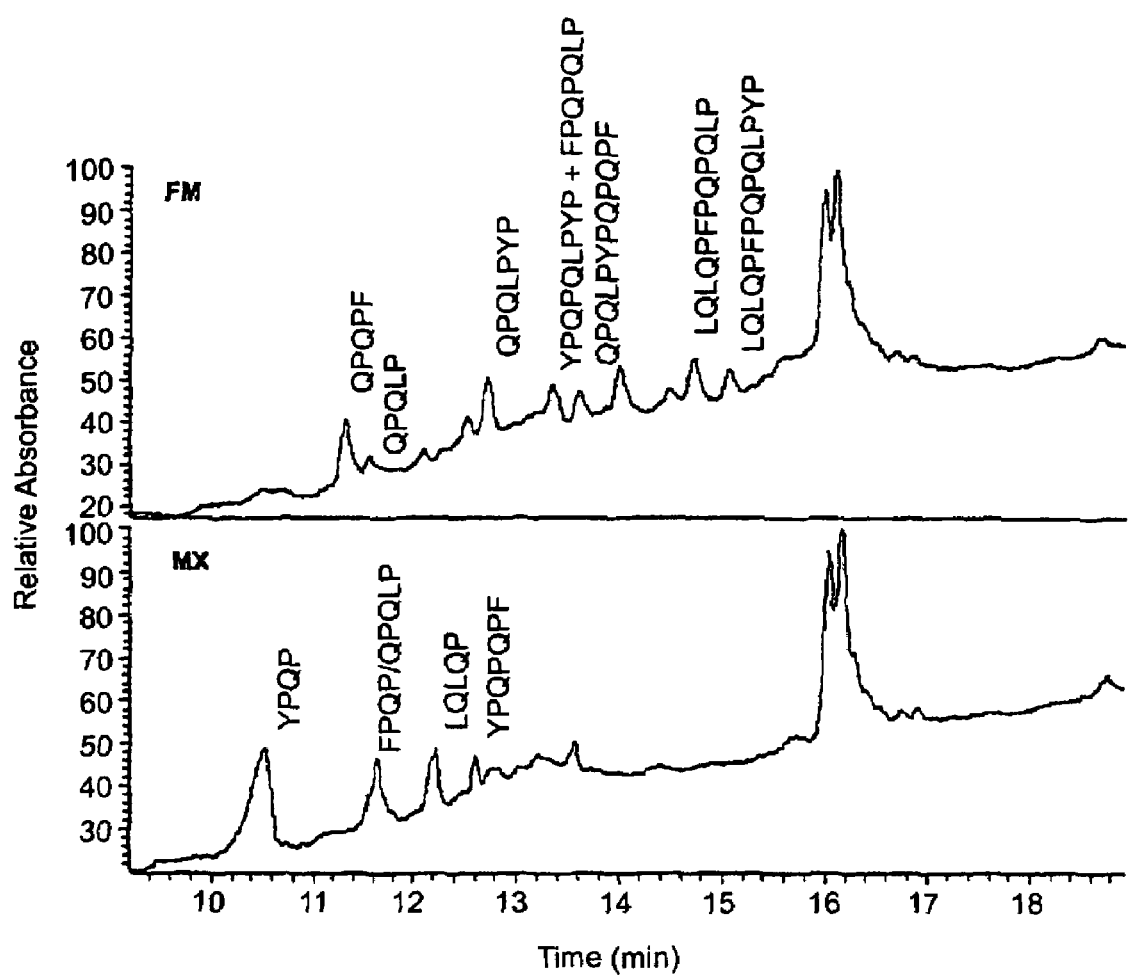

FIGS. 4A-4C. Hydrolysis of (SEQ ID NO:12) LQLQPF-PQPQLPYPQPQLPYP QPQLPYPQPQPF by FM PEP, MX PEP and SC PEP. (A) Time dependence of hydrolysis in the presence of 10 µM substrate and 0.1 µM enzyme. The substrate appears as a doublet at a retention time of ca. 18 min, due to the presence of equal quantities of the 32-mer from which the N-terminal Leu is deleted; presence of this contaminant does not affect analysis. From the residual peak areas, the rates of substrate (33-mer+32-mer) disappearance were calculated as 2.3 µM/min (FM PEP), 0.43 µM/min (MX PEP) and 0.07 µM/min (SC PEP). (B) Initial cleavage fragments observed due to hydrolysis by FM PEP (t=1 min) and MX PEP (t=5 min). (C) Summary of initial cleavage fragments from FM PEP and MX PEP catalyzed hydrolysis of the 33-mer substrate.

Figure 5A:
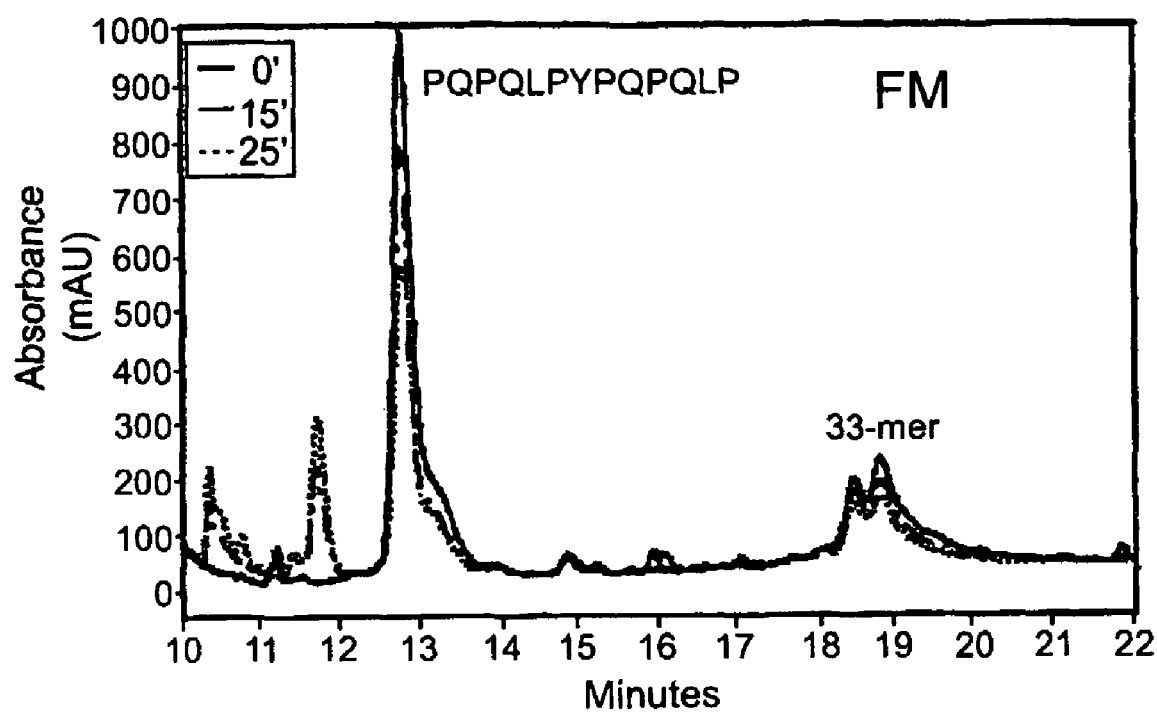
Figure 5B:
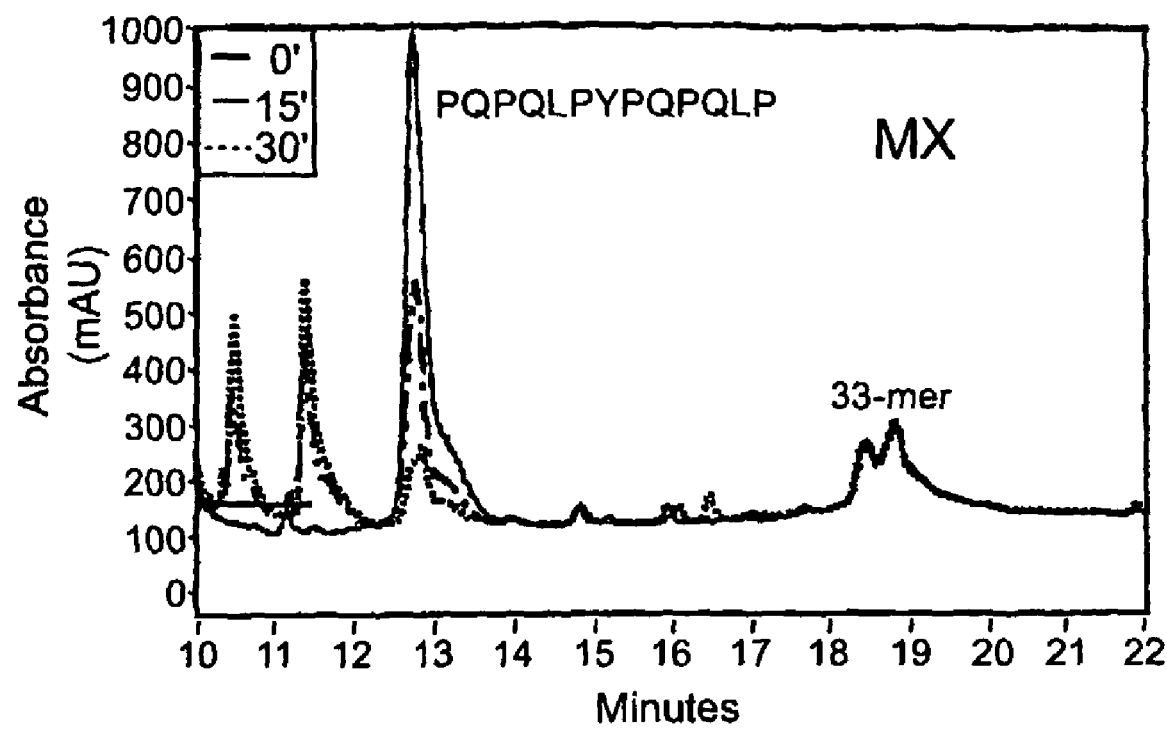
Figure 5C:
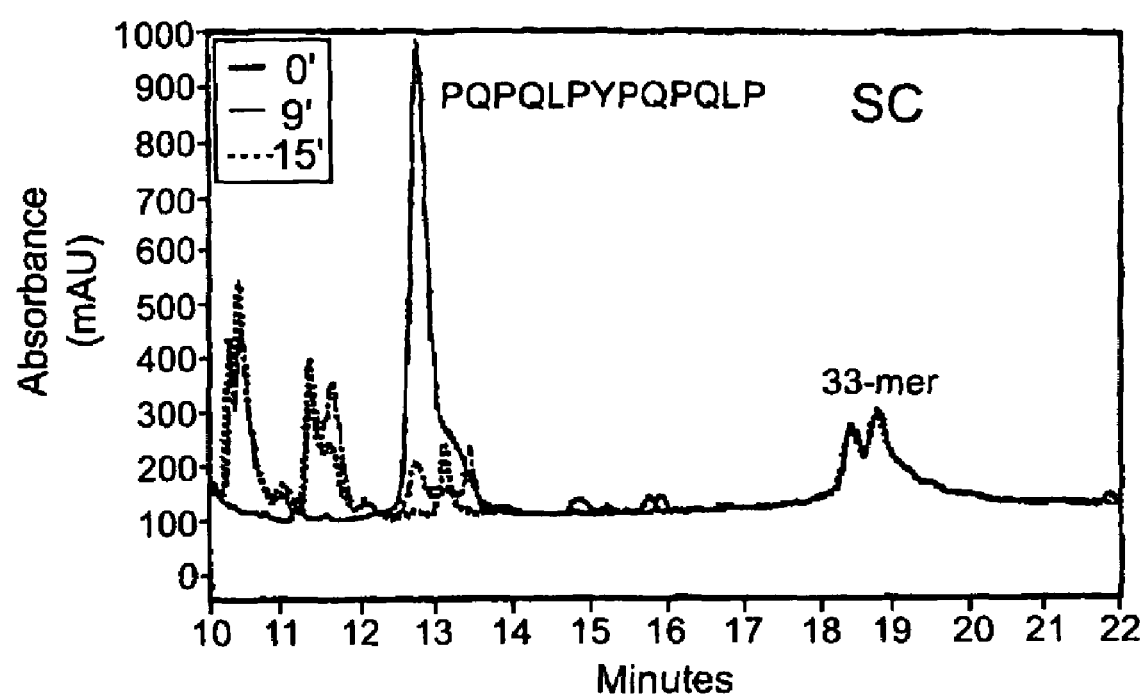

FIGS. 5A-5C. Competitive proteolysis of (SEQ ID NO:11) PQPQLPYPQPQLP and (SEQ ID NO:12) LQLQPF-PQPQLPYPQPQLPYPQPQPF by each PEP. 10 µM of the longer peptide and 50 µM of the shorter peptide were co-incubated with 0.1 µM of (A) FM PEP; (B) MX PEP; (C) SC PEP.

Figure 6:
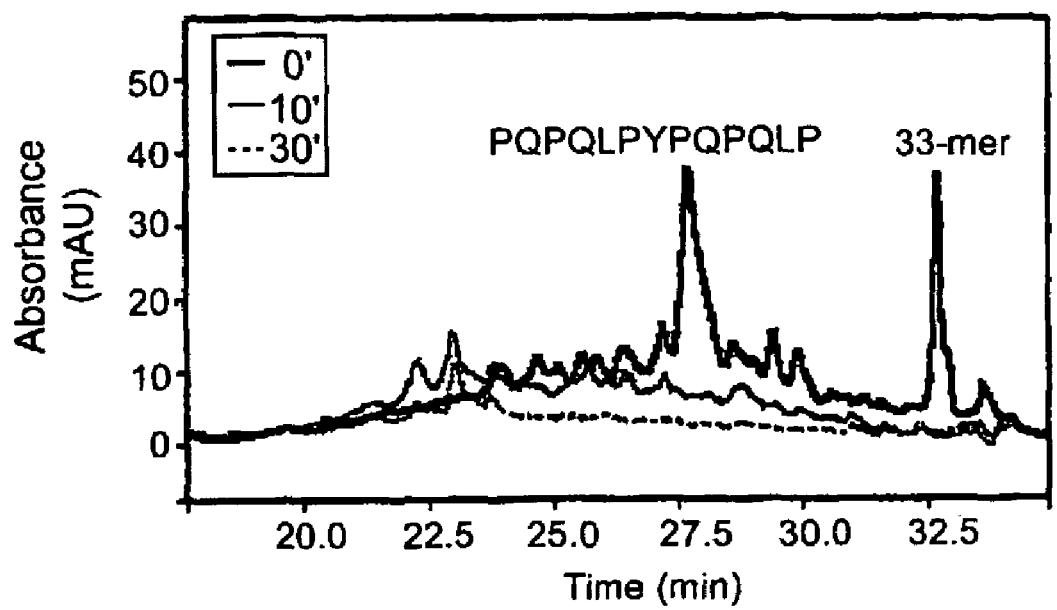
Figure 6:
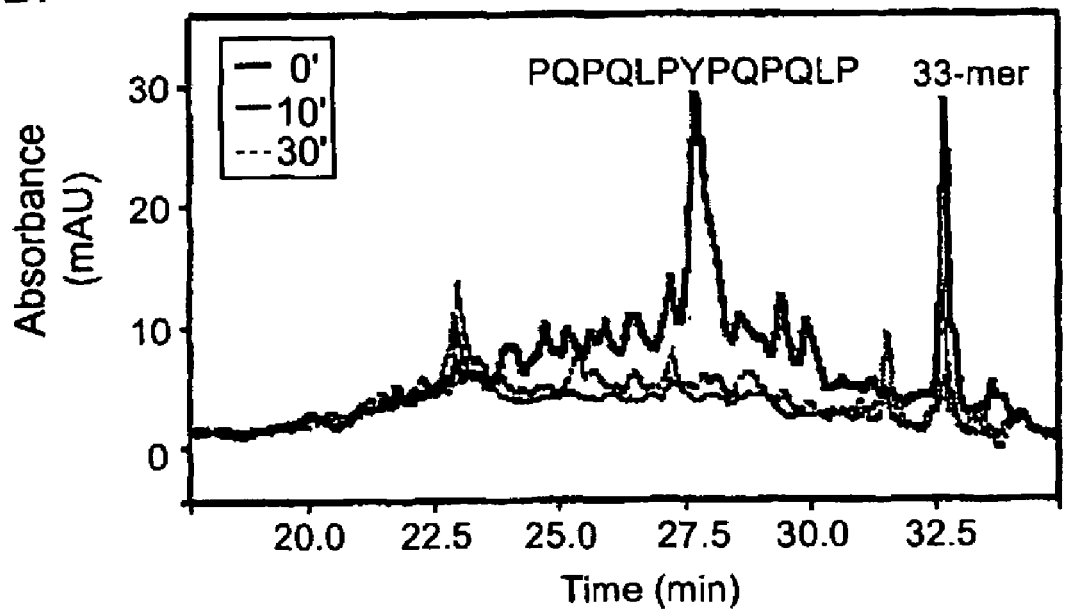

FIGS. 6A-6B. Competitive proteolysis of (SEQ ID NO:11) PQPQLPYPQPQLP (50 µM) and (SEQ ID NO:12) LQLQPFPQPQLPYPQPQLPYPQPQLPYPQPQPF (10 µM) in the presence of 30 mg/ml pepsin-treated gluten. This complex mixture of substrates was treated under physiological conditions with a mixture of pancreatic enzymes (trypsin, chymotrypsin, carboxypeptidase, elastase), brush border membrane enzymes (derived from rat small intestine) and either (A) FM PEP or (B) MX PEP.

Figure 7:
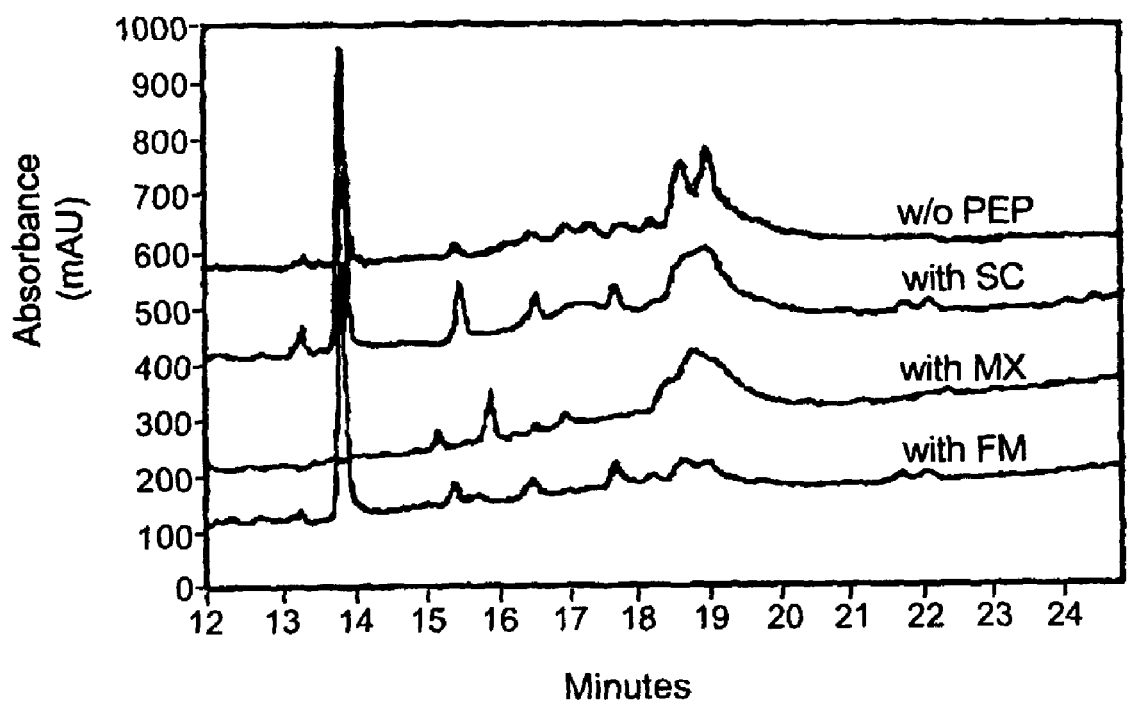

FIG. 7. (SEQ ID NO:12) Proteolysis of LQLQPF-PQPQLPYPQPQLPYPQPQL PYPQPQPF (5 µM) co-perfused with individual PEP's (0.1 µM) in the small intestinal lumen of an anesthetized rat. Each enzyme-substrate mixture was introduced via a catheter into a 15-20 cm segment of the upper jejunum. Samples were collected at the other end of the segment, and analyzed by UV-HPLC (215 nm). The control without any PEP is shown in the top trace.

DETAILED DESCRIPTION OF THE EMBODIMENTS

Glutenase enzymes and enzyme formulations are useful in the treatment of gluten intolerance. The enzymes decrease the levels of toxic gluten oligopeptides in foodstuffs, either prior to or after ingestion by a patient. Enzymes of interest include prolyl endopeptidases (PEP), e.g. the *Myxococcus xanthus* PEP; and endoproteases, e.g. *Hordeum vulgare* subsp. *vulgare* EPB2. Certain gluten oligopeptides known to be resistant to cleavage by gastric and pancreatic enzymes are digested by such enzymes, thereby preventing or relieving their toxic effects in patients. Gluten intolerance is associated primarily with Celiac Sprue and dermatitis herpetiformis, however it is also known in the art to be found in other patients, e.g. associated with autism. Such patients may also be treated with the methods of the invention.

In some patients, these methods and compositions allow the patient to ingest glutens without serious health consequences, much the same as individuals that do not suffer from either of these conditions. In some embodiments, the formulations of the invention comprise a glutenase contained in an enteric coating that allows delivery of the active agent(s) to the intestine; in other embodiments, the active agent(s) is stabilized to resist digestion in acidic stomach conditions. In some cases the active agent(s) have hydrolytic activity under acidic pH conditions, and can therefore initiate the proteolytic process on toxic gluten sequences in the stomach itself. Alternative methods of administration provided by the invention include genetic modification of patient cells, e.g. enterocytes, to express increased levels of glutenases; and the introduction of micro-organisms expressing such glutenases so as to transiently or permanently colonize the patient's intestinal tract. Such modified patient cells (which include cells that are not derived from the patient but that are not immunologically rejected when administered to the patient) and microorganisms of the invention are, in some embodiments, formulated in a pharmaceutically acceptable excipient, or introduced in foods. In another embodiment, the invention provides foods pretreated or combined with a glutenase and methods for treating foods to remove the toxic oligopeptides of gluten.

The compositions of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that may be treated by the methods of the invention include those diagnosed with celiac sprue through one or more of serological tests, e.g. anti-gliadin antibodies, anti-transglutaminase antibodies, anti-endomysial antibodies; endoscopic evaluation, e.g. to identify celiac lesions; histological assessment of small intestinal mucosa, e.g. to detect villous atrophy, crypt hyperplasia, infiltration of intra-epithelial lymphocytes; and any GI symptoms dependent on inclusion of gluten in the diet.

Given the safety of oral proteases, they also find a prophylactic use in high-risk populations, such as Type I diabetics, family members of diagnosed celiac patients, HLA-DQ2 positive individuals, and/or patients with gluten-associated symptoms that have not yet undergone formal diagnosis. Such patients may be treated with regular-dose or low-dose (10-50% of the regular dose) enzyme. Similarly, temporary high-dose use of such an agent is also anticipated for patients recovering from gluten-mediated enteropathy in whom gut function has not yet returned to normal, for example as judged by fecal fat excretion assays.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

As used herein, the term "glutenase" refers to an enzyme useful in the methods of the present invention that is capable, alone or in combination with endogenous or exogenously added enzymes, of cleaving toxic oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively. For further discussion of gluten proteins, see the review by Wieser (1996) Acta Paediatr Suppl. 412:3-9, incorporated herein by reference.

Enzymes

In one embodiment of the present invention, the glutenase enzyme is a PEP. Homology-based identification (for example, by a PILEUP sequence analysis) of prolyl endopeptidases can be routinely performed by those of skill in the art upon contemplation of this disclosure to identify PEPs suitable for use in the methods of the present invention. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningoscepticum*, *Aeromonas hydrophila*, *Aeromonas punctata*, *Novosphingobium capsulatum*, *Pyrococcus furiosus* and from mammalian sources are biochemically characterized PEPs. Others such as the *Nostoc* and *Arabidopsis* enzymes are likely to be PEPs but have not been fully characterized to date. Homologs of the enzymes of interest may be found in publicly available sequence databases, and the methods of the invention include such homologs. Candidate enzymes are expressed using standard heterologous expression technologies, and their properties are evaluated using the assays described herein.

In one embodiment of the invention, the glutenase is *Flavobacterium meningosepticum* PEP (GenBank ID # D10980). Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme. A variety of assays have verified the therapeutic utility of this PEP. In vitro, this enzyme has been shown to rapidly cleave several toxic gluten peptides, including the highly inflammatory 33-mer, (SEQ ID NO:12) LQLQPFPQPQLPYPQPQLPYPQPQLPYPQPQPF. In vivo it acts synergistically with the peptidases of the intestinal brush border membrane so as to rapidly detoxify these peptides, as well as gluten that has been pre-treated with gastric and pancreatic proteases. It has broad chain length specificity, making it especially well suited for the breakdown of long proline-rich peptides released into the duodenum from the stomach. The enzyme has a pH optimum around pH 7, and has high specific activity under conditions that mimic the weakly acidic environment of the upper small intestine. *Flavobacterium* PEP can cleave all T cell epitopes in gluten that have been tested to date. It has particular preference for the immunodominant epitopes found in alpha-gliadin. When grocery-store gluten is treated with this PEP, a rapid decrease in its antigenicity can be observed, as judged by LC-MS analysis and testing against polyclonal T cell lines derived from small intestinal biopsies from Celiac Sprue patients. The denatured protein is non-allergenic in rodents, rabbits and humans. It is relatively stable toward destruction by pancreatic proteases, an important feature since under physiological conditions it will be expected to act in concert with those enzymes.

Another enzyme of interest is *Sphingomonas capsulata* PEP (Genbank ID# AB010298). This enzyme is comparable to the *Flavobacterium* and *Myxococcus* enzyme. It has broader sequence specificity than either the *Flavobacterium* or the *Myxococcus* PEP, and may therefore be able to destroy the widest range of antigenic epitopes. Like the *Myxococcus* enzyme, it is also well expressed in *E. coli*.

Another enzyme of interest is *Penicillium citrinum* PEP (Genbank ID# D25535). This enzyme has been shown to possess PEP activity based on its ability to effectively cleave a number of Pro-Xaa bonds in peptides such as dynorphin A and substance P. The putative metalloprotease has the advantages of small size and a pH profile that renders it suitable to working in concert with the pancreatic enzymes in the duodenum. As such, it is a good candidate for the treatment of Celiac Sprue.

Another enzyme of interest is *Lactobacillus helveticus* PEP (Genbank ID# 321529). Unlike the above PEPs, this PEP is a zinc enzyme. It can efficiently proteolyze long peptide substrates such as the casein peptides SEQ ID NO:46 YQEPVLGPVRGPFPIIV and SEQ ID NO:47 RPKHPIKHQ. Proteolysis occurs at all PV and PI subsites, suggesting the PEP prefers hydrophobic residues at the S1' position, as are frequently found in gluten. Since the producer strain of *L. helveticus* CNRZ32 is commonly used in cheesemaking, this enzyme has desirable properties as a food-grade enzyme.

Another enzyme of interest is *Myxococcus xanthus* PEP (Genbank ID# AF127082). This enzyme possesses many of the advantages of the *Flavobacterium* PEP. It can cleave the 33-mer into small non-toxic peptides. Whereas the *Flavobacterium* enzyme appears to have a relatively strict preference for PQ bonds in gliadin peptides, the *Myxococcus* enzyme can cleave at PQ, PY and PF bonds, a feature that allows it to proteolyze a broader range of gluten epitopes. Compared to the *Flavobacterium* enzyme, it has equivalent stability toward the pancreatic proteases and superior stability toward acidic environments. The *Myxococcus* enzyme is well expressed in *E. coli*, making it feasible to produce this enzyme cheaply.

Glutenase enzyme fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac Sprue.

Modifications of interest that do not alter primary sequence include chemical derivatization of proteins, including, for example, acylation, e.g. lauryl, stearyl, myrsityl, decyl, etc. groups, PEGylation, esterification, or amidation. Such modifications may be used to increase the resistance of the enzyme toward proteolysis, e.g. by attachment of PEG sidechains or lauryl groups to surface lysines. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The amino acid sequence of a glutenase, e.g. a naturally occurring glutenase, can be altered in various ways known in the art to generate targeted changes in sequence and additional glutenase enzymes useful in the formulations and compositions of the invention. Such variants will typically be functionally-preserved variants, which differ, usually in sequence, from the corresponding native or parent protein but still retain the desired biological activity. Variants also include fragments of a glutenase that retain enzymatic activity. Various methods known in the art can be used to generate targeted changes, e.g. phage display in combination with random and targeted mutations, introduction of scanning mutations, and the like.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

Various modifications may be made to the enzyme sequence. The MX PEP has a similar structure as that from the porcine muscle or brain. The enzyme consists of a catalytic domain with a typical α/β hydrolase fold, which is covalently connected to a cylindrical barrel-shaped propeller domain. The catalytic domain is made up of N-terminal residues 1-67 and C-terminal residues 410-678; the propeller domain includes residues 71-406. Two linear strands formed by residues 67-70 and 407-409 covalently connect the two domains. This analysis of the *M. xanthus* PEP is useful in the design of modified enzymes. Typically such modified enzymes will retain the catalytic triad (Ser 533, Asp 616 and His 651) as well as the conserved Arg 618 residues, all of which are expected to be important for activity. Residues Asn534, Tyr453 and Arg618 are conserved in the prolyl endopeptidase family, and such residues may also be conserved in the design of modified enzymes. In one embodiment, the extended region of the propeller domain is replaced with a short flexible linker, e.g. comprised of 5-10 Gly residues, thereby truncating the protein and reducing its proteolytic susceptibility to pepsin For example, mutations have been made with V458 and G532, which are close to the catalytic Ser533 in the binding pocket. Their mutants retain wild-type activity toward Suc-Ala-Pro-pNA, but show reduced activity toward the 13-mer. Other mutants, R572A/Q, I575A and F229Y have an increased specificity for a longer substrate.

Enzymes modified to provide for a specific characteristic of interest may be further modified, for e.g. by mutagenesis, exon shuffling, etc., as known in the art, followed by screening or selection, so as to optimize or restore the activity of the enzyme, e.g. to wild-type levels.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al., (2000) *J. Biol. Chem.* 275:23783-23789). Analogs of such proteins include those containing residues other than naturally occurring L-amino acids, e.g. D-amino acids or non-naturally occurring synthetic amino acids.

The glutenase proteins useful in the practice of the present invention may also be isolated and purified in accordance with conventional methods from recombinant production systems and from natural sources. Protease production can be achieved using established host-vector systems in organisms such as *E. coli, S. cerevisiae, P. pastoris, Lactobacii, Bacilli* and *Aspergilli*. Integrative or self-replicative vectors may be used for this purpose. In some of these hosts, the protease is expressed as an intracellular protein and subsequently purified, whereas in other hosts the enzyme is secreted into the extracellular medium. Purification of the protein can be performed by a combination of ion exchange chromatography, Ni-affinity chromatography (or some alternative chromatographic procedure), hydrophobic interaction chromatography, and/or other purification techniques. Typically, the compositions used in the practice of the invention will comprise at least 20% by weight of the desired product, more usually at least about 50% by weight, preferably at least about 85% by weight, at least about 90%, and for therapeutic purposes, may be at least about 95% by weight, in relation to contaminants related to the method of preparation of the product and its purification. Usually, the percentages will be based upon total protein. Proteins in such compositions may be present at a concentration of at least about 500 μg/ml; at least about 1 mg/mg; at least about 5 mg/ml; at least about 10 mg/ml, or more.

In one aspect, the present invention provides a purified preparation of a glutenase. Such enzymes may be produced by recombinant methods. In one embodiment, such methods utilize a bacterial host for expression, although fungal and eukaryotic systems find use for some purposes. Coding sequences that contain a signal sequence, or that are engineered to contain a signal sequence can be secreted into the periplasmic space of a bacterial host. An osmotic shock protocol can then be used to release the periplasmic proteins into the supernatant.

Where the enzyme is a cytoplasmic enzyme, a signal sequence can be introduced for periplasmic secretion, or the enzyme can be isolated from a cytoplasmic lysate. Methods for purification include Ni-NTA affinity purification, e.g. in combination with introduction of a histidine tag; and chromatography methods known in the art, e.g. cation exchange, anion exchange, gel filtration, HPLC, FPLC, and the like.

For various purposes, such as stable storage, the enzyme may be lyophilized. Lyophilization is preferably performed on an initially concentrated preparation, e.g. of at least about 1 mg/ml. Peg may be added to improve the enzyme stability. It has been found that MX PEP can be lyophilized without loss of specific activity. The lyophilized enzyme and excipients is useful in the production of enteric-coated capsules or tablets, e.g. a single capsule or tablet may contain at least about 1 mg. PEP, usually at least about 10 mg PEP, and may contain at least 100 mg PEP, at least about 500 mg PEP, or more. As described in detail here, enteric coatings may be applied, where a substantial fraction of the activity is retained, and is stable for at least about 1 month at 4° C. It has also been found that MX PEP retains activity in a tablet formulation.

Prior to the present invention, there was no perceived need for a glutenase that could be ingested by a human or mixed with a foodstuff. Thus, prior to the present invention most glutenases did not exist in a form free of contaminants that could be deleterious to a human if ingested. The present invention creates a need for such glutenase preparations and provides them and methods for preparing them. In a related embodiment, the present invention provides novel foodstuffs that are derived from gluten-containing foodstuffs but have been treated to reduce the concentration and amount of the oligopeptides and oligopeptide sequences discovered to be toxic to Celiac Sprue patients. While gluten-free or reduced-gluten content foods have been made, the foodstuffs of the present invention differ from such foodstuffs not only by the manner in which they are prepared, by treatment of the foodstuff with a glutenase, but also by their content, as the methods of the prior art result in alteration of non-toxic (to Celiac Sprue patients) components of the foodstuff, resulting in a different taste and composition. Prior art foodstuffs include, for example, Codex Alimentarius wheat starch, which is available in Europe and has <100 ppm gluten. The starch is usually prepared by processes that take advantage of the fact that gluten is insoluble in water whereas starch is soluble.

In one embodiment, the term "glutenase" as used herein refers to a protease or a peptidase enzyme that meets one or more of the criteria provided herein. Such critera also find use in the evaluation of enzyme modifications, e.g. as a screening tool following generation of modification. In some embodiments, modifications to the MX PEP amino acid sequence or non-peptidic modifications are assessed using such assays. Using these criteria, one of skill in the art can determine the suitability of a candidate enzyme or enzyme modification for use in the methods of the invention. Many enzymes will meet multiple criteria, including two, three, four or more of the criteria, and some enzymes will meet all of the criteria. The terms "protease" or "peptidase" can refer to a glutenase and as used herein describe a protein or fragment thereof with the capability of cleaving peptide bonds, where the scissile peptide bond may either be terminal or internal in oligopeptides or larger proteins. Prolyl-specific peptidases are glutenases useful in the practice of the present invention.

Glutenases of the invention include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. capsulata* (Genbank accession number AB010298), DCP I from rabbit (Genbank accession number X62551), DPP IV from *Aspergillus fumigatus* (Genbank accession number U87950), carboxypeptidase from *Aspergillus saitoi* (GenBank ID# D25288), PEP from *Lactobacillus helveticus* (Genbank ID# 321529) or cysteine proteinase B from *Hordeum vulgare* (Genbank accession number JQ1110).

Each of the above proteases described herein can be engineered to improve desired properties such as enhanced specificity toward toxic gliadin sequences, improved tolerance for longer substrates, acid stability, pepsin resistance, resistance to proteolysis by the pancreatic enzymes and improved shelf-life. The desired property can be engineered via standard protein engineering methods.

Other than proline, glutamine residues are also highly prevalent in gluten proteins. The toxicity of gluten in Celiac Sprue has been directly correlated to the presence of specific Gln residues. Therefore, glutamine-specific proteases are also beneficial for the treatment of Celiac Sprue . Since oats contain proteins that are rich in glutamine but not especially rich in proline residues, an additional benefit of a glutamine-specific protease is the improvement of oat tolerance in those celiac patients who show mild oat-intolerance. An example of such a protease is the above-mentioned cysteine endoproteinase from gluten. This enzyme cleaves gluten proteins rapidly with a distinct preference for post-Gln cleavage. Also of interest is *Hordeum vulgare* endoprotease (Genbank accession U19384), which has been shown to efficiently digest α2-gliadin. The enzyme is active under acidic conditions, and is useful as an orally administered dietary supplement. A gluten-containing diet may be supplemented with orally administered proEPB2, resulting in effective degradation of immunogenic gluten peptides in the acidic stomach, before these peptides enter the intestine and are presented to the immune system. Proteins with high sequence similarity to this enzyme are also of interest. An advantage of these enzymes is that they are considered as safe for human oral consumption, due to their presence in dietary gluten from barley.

Intestinal dipeptidyl peptidase IV and dipeptidyl carboxypeptidase I are the rate-limiting enzymes in the breakdown of toxic gliadin peptides from gluten. These enzymes are bottlenecks in gluten digestion in the mammalian small intestine because (i) their specific activity is relatively low compared to other amino- and carboxy-peptidases in the intestinal brush border; and (ii) due to their strong sensitivity to substrate chain length, they cleave long immunotoxic peptides such as the 33-mer extremely slowly. Both these problems can be ameliorated through the administration of proline-specific amino- and carboxy-peptidases from other sources. For example the X-Pro dipeptidase from *Aspergillus oryzae* (GenBank ID# BD191984) and the carboxypeptidase from *Aspergillus saitoi* (GenBank ID# D25288) can improve gluten digesion in the Celiac intestine.

A glutenase of the invention includes a peptidase or protease that has a specific activity of at least 2.5 U/mg, preferably 25 U/mg and more preferably 250 U/mg for cleavage of a peptide comprising one of more of the following motifs: Gly-Pro-pNA, Z-Gly-Pro-pNA (where Z is a benzyloxycarbonyl group), and Hip-His-Leu, where "Hip" is hippuric acid, pNA is para-nitroanilide, and 1 U is the amount of enzyme required to catalyze the turnover of 1 μmole of substrate per minute. Chromogenic substrates may be utilized in screening, e.g. substrates such as Cbz-Gly-Pro-pNA or Suc-Ala-Pro-pNA enables identification of proline-specific proteases. Similar substrates can also be used to identify glutamine-specific proteases. These assays can be monitored by UV-Vis spectrophotometric methods.

A glutenase of the invention includes an enzyme belonging to any of the following enzyme classifications: EC 3.4.21.26, EC 3.4.14.5, or EC 3.4.15.1.

A glutenase of the invention includes an enzyme having a kcat/Km of at least about 2.5 s$^{-1}$ M$^{-1}$, usually at least about 250 s$^{-1}$ M$^{-1}$: and preferably at least about 25000 s$^{-1}$ M$^{-1}$ for cleavage of any of the following peptides, including known T cell epitopes in gluten, under optimal conditions: (SEQ ID NO:1) QLQPFPQPQLPY or (SEQ ID NO:37) PFPQPQLPY, (SEQ ID NO:3) PQPQLPYPQPQLPY or (SEQ ID NO:38) PQPQLPYPQ, (SEQ ID NO:13) QPQQSFPQQQ or (SEQ ID NO:39) PQQSFPQQQ, (SEQ ID NO:14) QLQPF-PQPELPY, (SEQ ID NO:15) PQPELPYPQPELPY, (SEQ ID NO:16) QPQQSFPEQQ; (SEQ ID NO: 30) IQPQQPAQL; (SEQ ID NO:31) QQPQQPYPQ; (SEQ ID NO:32) SQPQQQFPQ; (SEQ ID NO:33) QQPFPQQPQ; or (SEQ ID NO:34) PFSQQQQPV. Cleavage of longer, physiologically generated peptides containing one or more of the above epitopes may also be assessed, for example cleavage of the 33-mer from alpha-gliadin, (SEQ ID NO:12) LQLQPF (PQPQLPY)$_3$PQPQPF, and the 26-mer from gamma-gliadin, (SEQ ID NO:35) FLQPQQPFPQQPQQPYPQQPQQPFPQ. A glutenase of the invention includes peptidase or protease having a specificity kcat/Km>2 mM$^{-1}$s$^{-1}$ for the quenched fluorogenic substrate (SEQ ID NO:36) Abz-QPQQP-Tyr (NO$_2$)-D. These assays can be monitored by HPLC or fluorescence spectroscopy. For the latter assays, suitable fluorophores can be attached to the amino- and carboxy-termini of the peptides.

A glutenase useful in the practice of the present invention can be identified by its ability to cleave a pretreated substrate to remove toxic gluten oligopeptides, where a "pretreated substrate" is a gliadin, hordein, secalin or avenin protein that has been treated with physiological quantities of gastric and pancreatic proteases, including pepsin (1:100 mass ratio), trypsin (1:100), chymotrypsin (1:100), elastase (1:500), and carboxypeptidases A and B (1:100). Pepsin digestion may be performed at pH 2 for 20 min., to mimic gastric digestion, followed by further treatment of the reaction mixture with trypsin, chymotrypsin, elastase and carboxypeptidase at pH 7 for 1 hour, to mimic duodenal digestion by secreted pancreatic enzymes. The pretreated substrate comprises oligopeptides resistant to digestion, e.g. under physiological conditions. A glutenase may catalyze cleavage of pepsin-trypsin-chymotrypsin-elastase-carboxypeptidase (PTCEC) treated gluten such that less than 10% of the products are longer than (SEQ ID NO:3, aa 1-9) PQPQLPYPQ (as judged by longer retention times on a C18 reverse phase HPLC column monitored at A$_{215}$).

The ability of a peptidase or protease to cleave a pretreated substrate can be determined by measuring the ability of an enzyme to increase the concentration of free NH$_2$-termini in a reaction mixture containing 1 mg/ml pretreated substrate and 10 μg/ml of the peptidase or protease, incubated at 37° C. for 1 hour. A glutenase useful in the practice of the present invention will increase the concentration of the free amino termini under such conditions, usually by at least about 25%, more usually by at least about 50%, and preferably by at least about 100%. A glutenase includes an enzyme capable of reducing the residual molar concentration of oligopeptides greater than about 1000 Da in a 1 mg/ml "pretreated substrate" after a 1 hour incubation with 10 μg/ml of the enzyme by at least about 2-fold, usually by at least about 5-fold, and preferably by at least about 10-fold. The concentration of such oligopeptides can be estimated by methods known in the art, for example size exclusion chromatography and the like.

A glutenase of the invention includes an enzyme capable of detoxification of whole gluten, as monitored by polyclonal T cell lines derived from intestinal biopsies of celiac patients; detoxification of whole gluten as monitored by LC-MS-MS; and/or detoxification of whole gluten as monitored by ELISA assays using monoclonal antibodies capable of recognizing sequences specific to gliadin.

For example, a glutenase may reduce the potency by which a "pretreated substrate" can antagonize binding of (SEQ ID NO:17) PQPELPYPQPQLP to HLA-DQ2. The ability of a substrate to bind to HLA-DQ is indicative of its toxicity; fragments smaller than about 8 amino acids are generally not stably bound to Class II MHC. Treatment with a glutenase that digests toxic oligopeptides, by reducing the concentration of the toxic oligopeptides, prevents a mixture containing them from competing with a test peptide for MHC binding. To test whether a candidate glutenase can be used for purposes of the present invention, a 1 mg/ml solution of "pretreated substrate" may be first incubated with 10 μg/ml of the candidate glutenase, and the ability of the resulting solution to displace radioactive (SEQ ID NO:18) PQPELPYPQPQPLP pre-bound to HLA-DQ2 molecules can then be quantified, with a reduction of displacement, relative to a non-treated control, indicative of utility in the methods of the present invention.

A glutenase of the invention includes an enzyme that reduces the anti-tTG antibody response to a "gluten challenge diet" in a Celiac Sprue patient by at least about 2-fold, more usually by at least about 5-fold, and preferably by at least about 10-fold. A "gluten challenge diet" is defined as the intake of 100 g bread per day for 3 days by an adult Celiac Sprue patient previously on a gluten-free diet. The anti-tTG antibody response can be measured in peripheral blood using standard clinical diagnostic procedures, as known in the art.

Excluded from the term "glutenase" are the following peptidases: human pepsin, human trypsin, human chymotrypsin, human elastase, papaya papain, and pineapple bromelain, and usually excluded are enzymes having greater than 98% sequence identity at the amino acid level to such peptidases, more usually excluded are enzymes having greater than 90% sequence identity at the amino acid level to such peptidases, and preferably excluded are enzymes having greater than 70% sequence identity at the amino acid level to such peptidases.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Eng* (New York) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. In one aspect of the present invention, genetically modified plants are provided that differ from their naturally occurring counterparts by having gliadin proteins that contain a reduced content of glutamine and proline residues.

Examples of gliadin sequences include but are not limited to wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1;

U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal human digestion of gliadins and related storage proteins as described above, from dietary cereals, e.g. wheat, rye, barley, and the like. Such oligopeptides are believed to act as antigens for T cells in *Celiac Sprue*. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO:8). Determination of whether an oligopeptide is immunogenic for a particular patient is readily determined by standard T cell activation and other assays known to those of skill in the art.

As demonstrated herein, during digestion, peptidase resistant oligopeptides remain after exposure of glutens, e.g. gliadin, to normal digestive enzymes. Examples of peptidase resistant oligopeptides are provided, for example, as set forth in SEQ ID NO:5, 6, 7 and 10. Other examples of immunogenic gliadin oligopeptides are described in Wieser (1995) Baillieres Clin Gastroenterol 9(2):191-207, incorporated herein by reference.

Determination of whether a candidate enzyme will digest a toxic gluten oligopeptide, as discussed above, can be empirically determined. For example, a candidate may be combined with an oligopeptide comprising one or more Gly-Pro-pNA, Z-Gly-Pro-pNA, Hip-His-Leu, (SEQ ID NO:40) Abz-QLP-Tyr(NO$_2$)-PQ, (SEQ ID NO:42 PQP-Lys(Abz)-LP-Tyr (NO$_2$)-PQPQLP, (SEQ ID NO:43) PQPQLP-Tyr(NO$_2$)-PQP-Lys(Abz)-LP motifs; with one or more of the oligopeptides (SEQ ID NO:1) QLQPFPQPQLPY, (SEQ ID NO:3) PQPQLPYPQPQLPY, (SEQ ID NO:13) QPQQSF-PQQQ, (SEQ ID NO:14) QLQPFPQPELPY, (SEQ ID NO:15) PQPELPYPQPELPY, (SEQ ID NO:16) QPQQSF-PEQQ or (SEQ ID NO:12) LQLQPF-PQPQLPYPQPQLPYPQPQLPYPQPQPF; or with a pretreated substrate comprising one or more of gliadin, hordein, secalin or avenin proteins that have been treated with physiological quantities of gastric and pancreatic proteases. In each instance, the candidate is determined to be a glutenase of the invention if it is capable of cleaving the oligopeptide. Glutenases that have a low toxicity for human cells and are active in the physiologic conditions present in the intestinal brush border are preferred for use in some applications of the invention, and therefore it may be useful to screen for such properties in candidate glutenases.

The oligopeptide or protein substrates for such assays may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Recombinant DNA technology can also be used to produce the peptide.

The level of digestion of the toxic oligopeptide can be compared to a baseline value. The disappearance of the starting material and/or the presence of digestion products can be monitored by conventional methods. For example, a detectable marker can be conjugated to a peptide, and the change in molecular weight associated with the marker is then determined, e.g. acid precipitation, molecular weight exclusion, and the like. The baseline value can be a value for a control sample or a statistical value that is representative a control population. Various controls can be conducted to ensure that an observed activity is authentic, including running parallel reactions, positive and negative controls, dose response, and the like.

Active glutenases identified by the screening methods described herein can serve as lead compounds for the synthesis of analog compounds to identify glutenases with improved properties. Identification of analog compounds can be performed through use of techniques such as self-consistent field (SCF) analysis, configuration interaction (CI) analysis, and normal mode dynamics analysis.

A desirable property in glutenases is stability against gastric (low pH and pepsin) conditions. Glutenases with enhanced gastric stability can be identified by mutagenesis, followed colony transfer to liquid culture in high-throughput screening formats such as 96-well plates. Following growth, a fraction of the cell culture can be lysed and the lysate incubated for variable durations under simulated gastric conditions (pepsin, pH 2). Thereafter, the lysate can be assayed with a suitable chromogenic substrate (e.g. Cbz-Succinyl-Ala-Pro-pNA). An intense yellow color will develop in the presence of extracts with enhanced gastric stability.

Formulations

In one embodiment of the present invention, a Celiac Sprue patient is, in addition to being provided a glutenase or food treated in accordance with the present methods, provided an inhibitor of tissue transglutaminase, an anti-inflammatory agent, an anti-ulcer agent, a mast cell-stabilizing agents, and/or and an-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the glutenases and treated foodstuffs of the invention can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

The glutenase proteins of the invention and/or the compounds administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the glutenase and/or other compounds can be achieved in various ways, usually by oral administration. The glutenase and/or other compounds may be systemic after administration or may be localized by virtue of the formulation, or by the use of an implant that acts to retain the active dose at the site of implantation.

In pharmaceutical dosage forms, the glutenase and/or other compounds may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. A number of methods are available in the art for the efficient delivery of enterically coated proteins into the small intestinal lumen. Most methods rely upon protein release as a result of the sudden rise of pH when food is released from the stomach into the duodenum, or upon the action of pancreatic proteases that are secreted into the duodenum when food enters the small intestine. For intestinal delivery of a PEP and/or a glutamine specific protease, the enzyme is usually lyophilized in the presence of appropriate buffers (e.g. phosphate, histidine, imidazole) and excipients (e.g. cryoprotectants such as sucrose, lactose, trehalose). Lyophilized enzyme cakes are blended with excipients, then filled into capsules, which are enterically coated with a polymeric coating that protects the protein from the acidic environment of the stomach, as well as from the action of pepsin in the stomach. Alternatively, protein microparticles can also be coated with a protective layer. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71 (3):307-18.

Gluten detoxification for a gluten sensitive individual can commence as soon as food enters the stomach, since the acidic environment (~pH 2) of the stomach favors gluten solubilization. Introduction of an acid-stable PEP or glutamine-specific protease into the stomach will synergize with the action of pepsin, leading to accelerated destruction of toxic peptides upon entry of gluten in the small intestines of celiac patients. In contrast to a PEP that acts in the small intestine, gastric enzymes need not be formulated with enteric coatings. Indeed, since several proteases (including the above-mentioned cysteine proteinase from barley) self-activate by cleaving the corresponding pro-proteins under acidic conditions. In one embodiment of the invention, the formulation comprises a pro-enzyme that is activated in the stomach.

In another embodiment, a microorganism, for example bacterial or yeast culture, capable of producing glutenase is administered to a patient. Such a culture may be formulated as an enteric capsule; for example, see U.S. Pat. No. 6,008,027, incorporated herein by reference. Alternatively, microorganisms stable to stomach acidity can be administered in a capsule, or admixed with food preparations.

In another embodiment, the glutenase is admixed with food, or used to pre-treat foodstuffs containing glutens. Glutenase present in foods can be enzymatically active prior to or during ingestion, and may be encapsulated or otherwise treated to control the timing of activity. Alternatively, the glutenase may be encapsulated to achieve a timed release after ingestion, e.g. in the intestinal tract.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, the glutenase may be administered in dosages of 0.01 mg to 500 mg/kg body weight per day, e.g. about 20 mg/day for an average person. Efficient proteolysis of gluten in vivo for an adult may require at least about 500 units of a therapeutically efficacious enzyme, usually at least about 1000 units, more usually at least about 2000 units, and not more than about 50,000 units, usually not more than about 20,000 units, where one unit is defined as the amount of enzyme required to hydrolyze 1 μmol Cbz-Gly-Pro-pNA (for PEP) or Cbz-Gly-Gln-pNA (for a glutamine-specific protease) per min under specified conditions. Most PEPs have specific activities in the range of 5-50 units/mg protein. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1 mg, or 0.5 mg. In combination therapy a comparable dose of the two enzymes may be given; however, the ratio will be influenced by the relative stability of the two enzymes toward gastric and duodenal inactivation.

Enzyme treatment of Celiac Sprue is expected to be most efficacious when administered before or with meals. However, since food can reside in the stomach for 0.5-2 h, and the primary site of action is expected to be in the small intestine, the enzyme could also be administered within 1 hour after a meal.

Optimal gluten detoxification in vivo can also be achieved by combining an appropriate gastric protease with a PEP that acts upon gluten peptides in the duodenum, in concert with pancreatic enzymes. This can be achieved by co-administration of two enzyme doses, e.g. two capsules/tablets; via co-formulation of the two enzymes in appropriate quantities; etc. Lyophilized duodenal PEP particles or granules can be protected by a suitable polymeric enteric coating that promotes enzyme release only in the duodenum. In contrast, release of the gastric protease will be initiated immediately upon consumption of the dosage form. Combination treatment involving a PEP and a complementary therapeutic agent, such as an inhibitor of the enzyme tissue transglutaminase, is also provided.

In some embodiments of the invention, formulations comprise a cocktail of selected proteases. Such combinations may achieve a greater therapeutic efficacy. In one combination formulation, *Flavobacterium* PEP and *Myxococcus* PEP are co-formulated or co-adminsitered, to allow for the destruction of a broader range of gluten antigenic peptides. Similarly, combination therapy with one or two PEPs from the above list with an acid-stable PEP or glutamine endoprotease can lead to more efficient gluten proteolysis in the stomach, thereby simplifying the task of gluten assimilation in the upper small intestine.

In another embodiment, the formulation or administration protocol combines a protease product and an inhibitor of transglutaminase 2 (TG2). Such formulations may have additional protection from gluten mediated enteropathy, as TG2 has been shown to have a significant pro-inflammatory effect on gluten peptides in the celiac gut. In particular, TG2 inhibitors containing halo-dihydroisoxazole, diazomethylketone or dioxoindole moieties are useful for this purpose.

In another embodiment, the protease or protease cocktail is administered and/or formulated with an anti-inflammatory agent, e.g. a statin; p38 MAP kinase inhibitor; anti-TNFα agent; etc.

Those of skill will readily appreciate that dose levels can vary as a function of the specific enzyme, the severity of the symptoms and the susceptibility of the subject to side effects. Some of the glutenases are more potent than others. Preferred dosages for a given enzyme are readily determinable by those of skill in the art by a variety of means. A preferred means is to measure the physiological potency of a given compound.

Other formulations of interest include formulations of DNA encoding glutenases of interest, so as to target intestinal cells for genetic modification. For example, see U.S. Pat. No. 6,258,789, herein incorporated by reference, which discloses the genetic alteration of intestinal epithelial cells.

Therapeutic Methods

The methods of the invention are used to treat foods to be consumed or that are consumed by individuals suffering from Celiac Sprue and/or dermatitis herpetiformis by delivering an effective dose of glutenase. If the glutenase is administered directly to a human, then the active agent(s) are contained in a pharmaceutical formulation. Alternatively, the desired effects can be obtained by incorporating glutenase into food products or by administering live organisms that express glutenase, and the like. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ(a1*0301, b1*0302)] are indicative of a susceptibility to the disease.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

This application is related to U.S. Provisional 60/565,668, filed Apr. 26, 2004; to U.S. Provisional application 60/357, 238 filed Feb. 14, 2002; to U.S. Provisional Application 60/380,761 filed May 14, 2002; to U.S. Provisional Application 60/392,782 filed Jun. 28, 2002; and to U.S. Provisional application No. 60/422,933, filed Oct. 31, 2002, to U.S. Provisional Application 60/428,033, filed Nov. 20, 2002, to U.S. Provisional Application 60/435,881, filed Dec. 20, 2002, and to U.S. Ser. No. 10/367,405, filed Feb. 14, 2004, each of which are herein specifically incorporated by reference.

EXAMPLES

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Comparison of PEP Activities

To gain insight into the similarities and differences between naturally occurring prolyl endopeptidases, we have systematically compared the properties of three homologous PEPs from different bacterial sources. Our studies have utilized two known recombinant PEPs from *Flavobacterium meningosepticum* (FM) and *Sphingomonas capsulata* (SC), respectively, and a novel PEP from *Myxococcus xanthus* (MX) that we have expressed for the first time as a heterologous recombinant protein. The enzymatic activities of these PEPs were quantitatively analyzed versus model substrates as well as two gluten-derived peptides with potential relevance to Celiac Sprue pathogenesis. In particular, we have probed the influence of substrate chain length, pH, pancreatic proteases and intestinal brush border peptidases on the activity of each PEP. Both in vivo and ex vivo experiments were performed as part of these studies.

Experimental Procedures

Cloning of PEP Genes. The PEP genes were amplified from the genomic DNA from the corresponding bacterial strains (*F. meningosepticum*: ATCC 13253; *S. capsulata*: ATCC 14666; *M. xanthus*: ATCC 25232). The sequence of the putative MX PEP is available from the NCBI database (Locus ID AAD31004). Oligonucleotides used for PCR amplification included: (SEQ ID NO:44) (1) FM first half: 5'-AAC CAA TCA TAT GAA GTA CAA CAA ACT TTC TGT G (NdeI), (SEQ ID NO:2) 5'-GAT AAA AAC GGA AAG CTT GTA AGG GC (HindIII); FM second half: (SEQ ID NO:45) 5'-GCC CTT ACA AGC TTT CCG TTT TTA TC (HindIII) and (SEQ ID NO:4) 5'-CCC TTA ATT TTC AM TTT TAG CTC GAG TTT ATG ATT TAT A (SacI); (2) SC first half: (SEQ ID NO:5) 5'-AGG ATA TCC ATA TGA AGA ACC GCT TGT GG (NdeI), (SEQ ID NO:6) 5'-GAC AAC CTC GM TCC GTC GGC ATT G (HinfI); SC second half: (SEQ ID NO:7) 5'-CAA TGC CGA CGG ATT CGA GGT TGT C (HinfI), (SEQ ID NO:8) 5'CGC GGG GAC CTC GAG TAG AAA CTG (SacI); (3) MX: (SEQ ID NO:9) 5'-CT CCC CAT ATG TCC TAC CCG GCG ACC (NdeI) and (SEQ ID NO:10) 5'-GTG GCG GCG CAG GGC CGC MG CTT CCC AAG CG (HindIII). The amplified genes were cloned into a pET28b plasmid (Novagen).

Expression and Purification of PEPs. Expression plasmids were introduced via transformation into BL21(DE3) cells. Transformants grown at 37° C., and induced in the presence of 100 µM IPTG at 22° C. overnight. Low temperature induction was found to improve the yield of active enzyme. All purification steps were performed at 4° C. unless noted otherwise. Since FM and SC PEP enzymes naturally possess a signal sequence, they are secreted into the periplasmic space of *E. coli*. A modified osmotic shock protocol (EMD Biosciences, Calif.) was therefore used to obtain an enriched protein lysate containing either PEP. Cell pellets (4 L of culture) were resuspended in 30 ml of 30 mM Tris-HCl, pH 8, 20% sucrose and 1 mM EDTA, and stirred slowly at room temperature for 10 min. The suspension was centrifuged at 10,000 g for 15 min, and the cell pellet was resuspended in ice-cold $dH_2O$ and stirred slowly on ice for 10 min. The shocked cells were then centrifuged again at 40,000-50000 g for 30 min. The supernatant containing the periplasmic proteins was treated for 1-2 h with 1 M NaCl solution (to a final concentration of 300 mM NaCl), 1 M imidazole solution (to a final concentration 5 mM imidazole) and 1 ml of Ni-NTA resin (Qiagen, Calif.). The crude protein was then loaded onto a column containing additional 1 ml of Ni-NTA resin. After thorough wash steps using the wash buffer (50 mM phosphate, 300 mM NaCl, pH 7.0) with 0-10 mM imidazole, the PEP was eluted with 150 mM imidazole, 50 mM phosphate, 300 mM NaCl, pH 8. FM PEP was further purified on a FPLC system (Amersham Pharmacia, N.J.) through a HiTrap-SP cation exchange column. Prior to application on the HiTrap-SP column, the protein was exchanged into 20 mM phosphate buffer (pH 7). Following injection, PEP was eluted with a salt gradient from 20 mM phosphate, pH 7 (buffer A) to 20 mM phosphate, 500 mM NaCl, pH 7 (buffer B) at a flow rate of 1 ml/min. MX PEP, a cytosolic protein, was initially purified from a whole-cell lysate via Ni-NTA affinity chromatography (as detailed above). The protein was further purified on a Superdex 200 gel filtration column (Amersham) with an isocratic gradient of 20 mM HEPES, 2 mM DTT, pH 7.0 at 1 ml/min.

Activity Assays. Post-proline cleavage activity was measured using Z-Gly-Pro-p-nitroanilide and Succinyl-Ala-Pro-p-nitroanilide (Bachem, Calif.). Z-Gly-Pro-pNA was dissolved in a PBS:water:dioxane (8:1.2:0.8) assay mixture. The concentration of Z-Gly-Pro-pNA was varied from 100-600 µM. Although the substrate Z-Gly-Pro-pNA was effective in detecting enzyme activity, its insolubility at higher concentrations precluded kinetic measurements under substrate-saturated conditions. In contrast, Succinyl-Ala-Pro-pNA, had the advantage of high water solubility at all pH values tested, and was therefore a preferred substrate for kinetic studies. Hydrolysis of Suc-Ala-Pro-pNA by FM, SC and MX PEPs was monitored in a reaction mixture (300 µl) consisting of 30 µl of 10×PBS buffer, a final concentration of 0.01-0.02 µM enzyme, and Suc-Ala-Pro-pNA (5 mM stock) at final concentrations ranging between 100 µM to 4 mM. The release of the p-nitroanilide was spectrophotometrically detected at a wavelength of 410 nm. The initial velocity of the reaction was determined by the increase in absorbance at 410 nm, which was used to calculate Km and Kcat according to the Michaelis-Menten relationship. For measurement of the influence of pH on the enzyme activity, a series of pH buffer solutions were prepared using citric acid and disodium phosphate for pH values from 3.0 to 6.0, and sodium phosphates for pH values from 7.0 to 8.0. Reaction mixtures (300 µl) consisted of 30 µl of 10× pH buffer, final concentration of 0.01 µM enzyme, and Suc-Ala-Pro-pNA to final concentrations between 100 µM to 4 mM.

pH Stability. The ability to retain enzyme activity after exposure to acidic environments was determined. Hydrochloric acid solutions (10 µl) at pH values ranging from 1.5 to 4.0 were mixed with 1 µl of enzyme for 10-20 min. The acidic mixtures were then neutralized with 40 µl of 10×PBS solution, 60 µl of 5 mM substrate to a final volume of 300 µl. The recovered enzyme activity was measured spectrophotometrically and compared with non-acid treated controls under identical conditions.

Gastric and Pancreatic Protease Stability. In a 96-well U-bottomed plate, 5 µL of 2× reaction buffer (40 mM $Na_2HPO_4$, pH=6.5 for pancreatic enzymes or 20 mM HCl for pepsin) was placed, and 1 µL of the degrading enzyme (either 1 mg/ml pepsin or a cocktail of 1 mg/ml trypsin, 1 mg/ml chymotrypsin, 0.2 mg/ml elastase and 0.2 mg/ml carboxypeptidase A) followed by 4 µL of PEP (5-10 U/ml) were added. The plate was incubated at 37° C. for various times (e.g. 0, 5, 10, 20 and 30 min), with 190 µL of PEP substrate solution (2 µl Z-Gly-Pro-p-nitroanilide (16.8 mg/ml in dioxane) 14 µl dioxane, 24 µl water, 150 µl 10 mM PBS buffer, pH=7.5) added to each well. Absorption was measured at 410 nm for 1 to 2 min every 10 s to assay residual activity. Each buffer also contained 5 mg/ml gluten. Untreated gluten was used for pepsin, whereas gluten previously proteolyzed with pepsin (0.01 M HCl, pH=2.0, 1:50 w/w, 2 h, 37° C.) was used for all other enzymes. Wells containing acid (pH=2.0) were neutralized by addition of 10 µL 0.1 M NaOH before addition of the PEP substrate. Enzyme activities are expressed as a percentage of the maximum activity, typically observed at the zero time point.

Substrate Specificity. In addition to the reference substrates above, enzyme specificity was also evaluated using two immunogenic peptides derived from the sequence of γ-gliadin proteins in gluten. Both peptides were synthesized using solid-phase peptide synthesis. The peptide (SEQ ID NO:11) PQPQLPYPQPQLP contains the immunodominant γ II-epitope, and is resistant to proteolysis by pepsin or any pancreatic enzyme. PEP specificity toward this substrate was assessed in a competitive assay in which 100 µM (SEQ ID NO:11) PQPQLPYPQPQLP and 100 µM Suc-Ala-Pro-pNA were mixed and reacted with 0.02 µM PEP at 25° C. The initial velocity of Suc-Ala-Pro-pNA cleavage was measured spectrophotometrically, whereas the initial velocity of (SEQ ID NO:11) PQPQLPYPQPQLP hydrolysis was determined via HPLC. The apparent specificity, kcat/KM, for the hydrolysis of (SEQ ID NO:11) PQPQLPYPQPQLP could be determined based on the known kcat/KM of the enzyme for Suc-Ala-Pro-pNA and the observed reaction rates of the two substrates. In addition to (SEQ ID NO: 11) PQPQLPYPQPQLP, PEP specificity for the more complex but physiologically relevant peptide (SEQ ID NO: 12) LQLQPFPQPQLPYPQPQLPYPQPQPF (33-mer) was also assessed. Proteolysis reactions were performed at 37° C. in PBS buffer with 5-100 µM peptide and 0.1 µM PEP for time periods of 1 min-4 hrs.

The decrease in substrate concentration as well as concomitant intermediate and product build-up were monitored with HPLC analysis. RP-HPLC was performed on a system consisting of Beckman or Rainin Dynamax SD-200, a Varian 340 UV detector set at 215 nm and 280 nm. Solvent A was $H_2O$ with 0.1% TFA and solvent B was acetonitrile with 0.1% TFA; gradient used: 0-5% B in 0-15 min, 5-30% B in 15-30', 30-100% B in 30-35 min, 100% B for 5'; flow 1 ml/min; separation was performed on a 4.6×150 mm reverse phase C-18 column (Vydac, Hesperia, Calif., USA). Samples were centrifuged for 10 min at 13,400 g, prior to injection of 10-100 µl. Both (SEQ ID NO:11) PQPQLPYPQPQLP as well as the 33-mer have multiple post-proline endoproteolytic sites. Thus, multiple peptides accumulate during the course of the reaction, some of which are secondary PEP substrates in themselves. Electrospray-Ion Trap-MS-MS coupled with a UV-HPLC (LCQ Classic/Surveyor, ThermoFinnigan, Calif.) was used to identify the preferred cleavage sites in (SEQ ID NO:11) PQPQLPYPQPQLP and the 33-mer.

For further evaluation of the proteolysis of the 33-mer and (SEQ ID NO:11) PQPQLPYPQPQLP in the appropriate physiological environment, gluten (30 g/L) was suspended in 0.01 M HCl (pH=2.0) and incubated in the presence of pepsin (600 mg/L) for 2 h at 37° C. The resulting solution was neutralized using 10 M NaOH and diluted to 10 g/L in a phosphate buffer (40 mM, pH 6.5). 25 µl of this suspension were then supplemented with the 33-mer (0.1 mg/ml), (SEQ ID NO:11) PQPQLPYPQPQLP (0.08 mM), trypsin (0.1 mg/ml), chymotrypsin (0.1 mg/ml), elastase (0.02 mg/ml), carboxypeptidase A (0.02 mg/ml). Prolyl endopeptidase (FM or MX; 1×: 500 mU/ml; 5×: 2.5 U/ml; 10×: 5 U/ml) and rat intestinal brush border surface membranes (BB, 1×: 40 mU/ml, 2×: 80 mU/ml, DPP IV activity) were added to a total volume of 150 µl. The mixture was incubated at 37° C. and 25 µl aliquots were taken at 0, 5, 10, 30 and 60 min and immediately heat deactivated.

To examine the chain length specificity of individual PEPs, we performed competitive reactions containing both gluten-derived peptides, subjected the reaction mixture to RP-HPLC, and monitored the disappearance of each substrate was monitored as a function of time. The peak areas of the 33-mer (32.5 min) and (SEQ ID NO:11) PQPQLPYPQPQLP (27.5 min) were integrated.

In Vivo Endopeptidase Activity. An adult (female or male) rat was anesthetized and maintained at 36-37° C. during the entire surgical procedure. The peritoneal cavity was opened, and a small incision was made at the beginning and the end of a 15-20 cm jejunum segment. Polyethylene catheters were inserted and secured into the two ends. The input catheter was connected with a pump-driven syringe filled with a solution. The jejunum segment was perfused initially with PBS buffer to remove any residual debris at a flow rate of 0.4 ml/min. Purified peptide solutions (peptide concentration ranges from 25-100 µM) were then perfused at 0.4 ml/min through the jejunum segment with a 10-40 min residence time. In the case of a co-perfusion, the input catheter is connected with two simultaneous syringes, one with a peptide solution and the other with the prolyl endopeptidase solution (concentration ranges from 50-500 µU/µl). Fluid from the output catheter was collected into small centrifuge tubes in dry ice for subsequent analysis. The collected digestive products were analyzed by HPLC on a C18 column.

Results

PEP Protein Expression. FM and SC PEPs have their own signal sequences, and were therefore expressed as secreted, soluble enzymes in the periplasmic space of *E. coli*. A simple freeze-thaw lysis procedure led to recovery of periplasmic protein without significant contamination by cytoplasmic proteins. In contrast, the MX PEP lacks a native signal sequence, and was therefore expressed as a cytoplasmic protein. PEP was purified from each lysate by Ni-NTA affinity purification, followed by a second chromatographic step. The yields of active FM, SC and MX PEPs were 1 mg/L, 60 mg/L and 30 mg/L, respectively. The purity of the various PEPs was determined by SDS-PAGE to be >90%.

Kinetic Analysis with Reference Substrates. The activity of each PEP was initially evaluated using the standard chromogenic substrate succinyl-Ala-Pro-pNA. Release of the p-nitroaniline was detected at 410 nm, and kinetic data was fitted to the Michaelis-Menten relationship. Succinyl-Ala-Pro-pNA was selected as a reference substrate instead of the more commonly used Z-Gly-Pro-pNA due to the low solubility of the latter substrate, which necessitated use of co-solvents. The calculated kcat and KM values of FM, MX and SC PEPs for succinyl-Ala-Pro-pNA are tabulated (Table 1). While these enzymes all exhibited comparable level activity to that of a serine protease, MX PEP has a higher specificity than the FM PEP, whereas SC PEP has an intermediate level of specificity (Table 2). The higher specificity of MX can be attributed mainly to its higher affinity for the substrate, as reflected in the $K_M$.

TABLE 1

Kinetic parameters for Succinyl-Ala-Pro-p-nitroanilide hydrolysis by FM PEP, MX PEP and SC PEP.

| | $K_{cat}(s^{-1})$ | $K_M$ (mM) | $K_{cat}/K_M$ (mM$^{-1}$/s$^{-1}$) |
|---|---|---|---|
| FM PEP | 33 | 0.91 | 37 |
| MX PEP | 51 | 0.35 | 146 |
| SC PEP | 144 | 2.1 | 67 |

TABLE 2

Specificity of FM PEP, MX PEP and SC PEP for the immunogenic gliadin peptide SEQ ID NO:11 PQPQLPYPQPQLP.

| | $K_{cat}/K_M$ (mM$^{-1}$/s$^{-1}$) |
|---|---|
| FM PEP | 178 |
| MX PEP | 548 |
| SC PEP | 492 |

Figure 1:
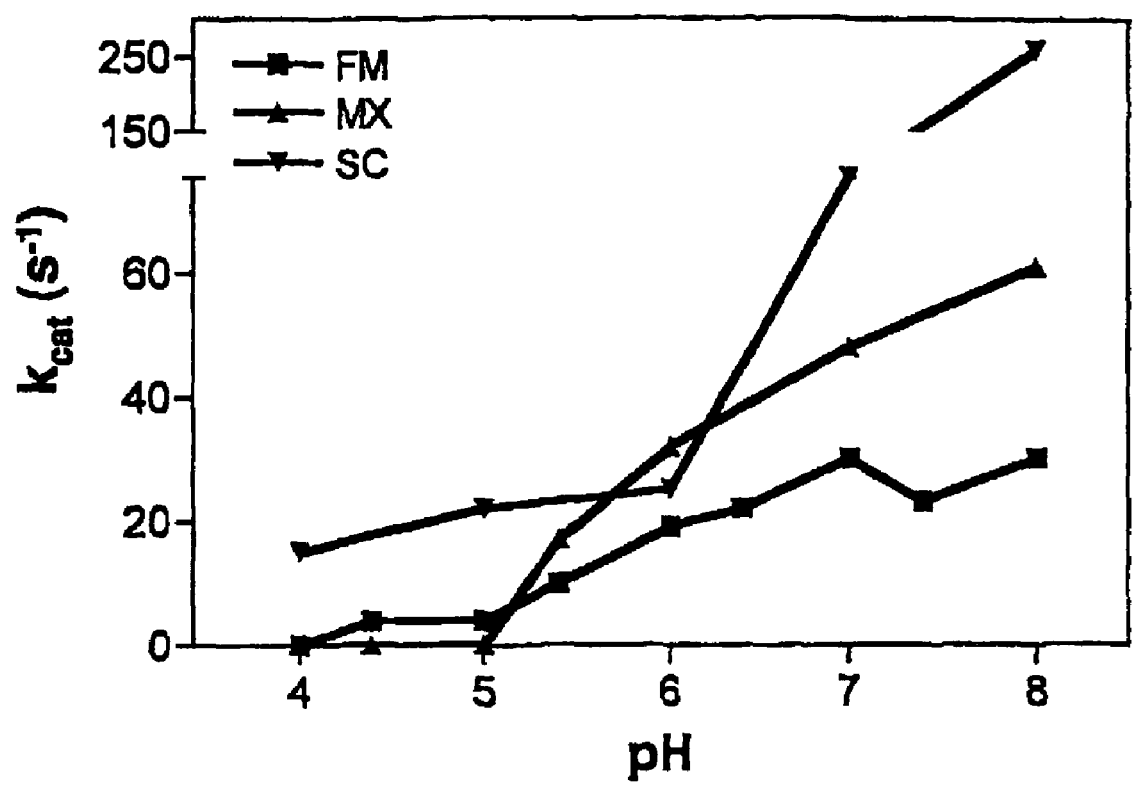
FIG. 1. Effect of pH on the turnover numbers (kcat) of FM PEP, MX PEP and SC PEP.

Enzyme Activity vs. pH. The luminal environment of the duodenum is approximately at pH 6. Therefore, a therapeutically useful PEP must retain high specific activity at that pH. The steady state turnover rate, kcat, of each PEP was titrated in various pH conditions using 100-4000 μM succinyl-Ala-Pro-pNA, shown in FIG. 1. Both FM PEP and MX PEP exhibited active site pKa around pH 6, indicating optimal activity in the pH 6-8 range. The diminished activity of both enzymes at pH 5 is consistent with the well-established role of a histidine residue as the general base in the serine protease catalytic triad, but alternatively it may indicate a change from the active enzyme conformation to an inactive state. Such conformational changes have been implicated in the catalytic cycle of the structurally characterized porcine brain PEP. Interestingly, the SC PEP, which has the broadest pH profile, shows a marked increase in maximum velocity under weakly basic conditions.

Figure 2:
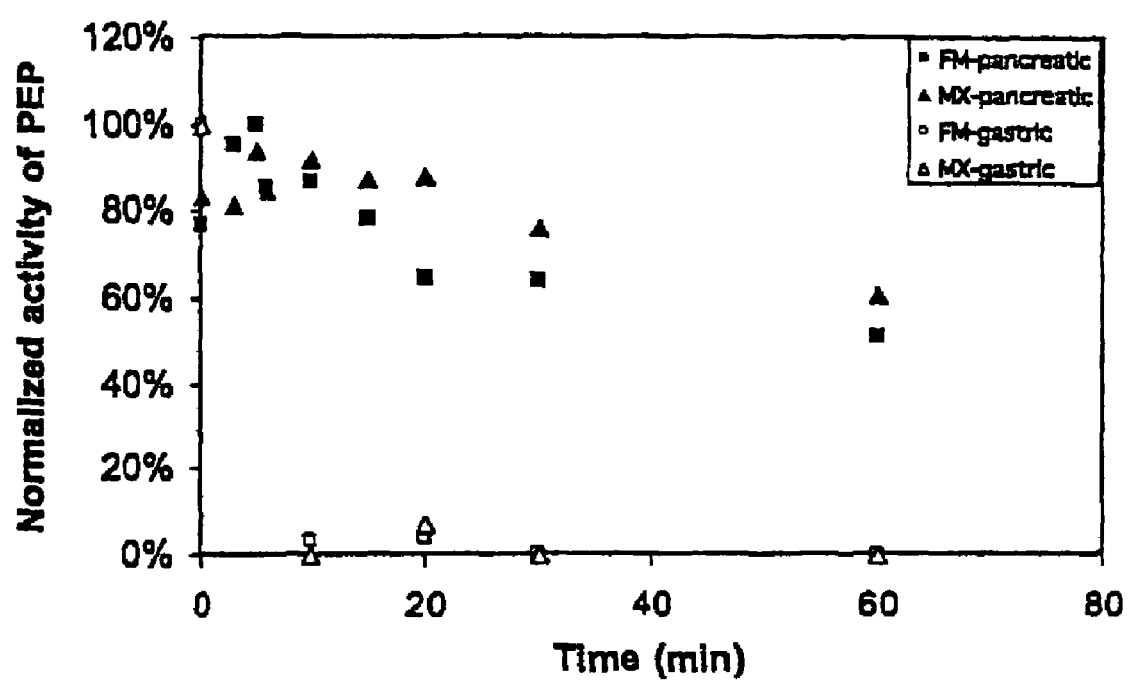
FIG. 2. Resistance of the FM PEP and the MX PEP to inactivation by gastric and pancreatic enzymes. Pancreatic enzyme stability was evaluated by treating 5 U/ml of the FM PEP and the MX PEP with 1 mg/ml trypsin, 1 mg/ml chymotrypsin, 0.2 mg/ml elastase and 0.2 mg/ml carboxypeptidase A (40 mM phosphate, pH=6.5). Pepsin stability was tested by treating the FM PEP and the MX PEP (5 U/ml) with 1 mg/ml pepsin (pH=2, 20 mM HCl).

PEP Stability. Although orally administered therapeutic proteins can be formulated to protect them from the acidic and proteolytic environment of the stomach, intrinsic acid stability of a PEP is likely to be a desirable characteristic in its use as a therapeutic agent for Celiac Sprue. We therefore evaluated the extent to which the activity of each PEP remains intact after 10 min of incubation at selected pH values between 1.6 and 3.9. Within this pH range, the FM PEP retained 50-70% of its original activity; the MX PEP retained 70-90% activity; and the SC PEP retained 30-80% activity. Thus, although all PEPs appear to be moderately acid-stable, the MX PEP is most versatile. Since therapeutic efficacy would require a PEP to act upon gluten in conjunction with pancreatic proteases that are secreted into the duodenum, the resistance of FM PEP and MX PEP toward both gastric and pancreatic enzymes was evaluated. For this we pre-incubated the enzymes with physiological quantities of either pepsin (at pH 2) or a cocktail comprising of trypsin, chymotrypsin, elastase and carboxypeptidase A (at pH 6.5). As can be seen in FIG. 2, both FM and MX PEP were highly susceptible to pepsin catalyzed proteolysis, whereas they appear to be remarkably stable to destruction in the presence of physiological quantities of the pancreatic enzymes.

Kinetic analysis using (SEQ ID NO: 11) PQPQLPYPQPQLP as a substrate. The immunogenic peptide (SEQ ID NO: 11) PQPQLPYPQPQLP is a recurring sequence in γ-gliadins, and is resistant to proteolysis by gastric and pancreatic proteases. It is also highly resistant to digestion by intestinal brush border peptidases, with only dipeptidyl carboxypeptidase I (DCP1) able to act upon it. Treatment of this peptide with PEP results in cleavage at internal proline residues, which in turn generates new recognition sites for brush border aminopeptidases. Thus, (SEQ ID NO:11) PQPQLPYPQPQLP represents a good test substrate to probe PEP specificity.

The $k_{cat}/K_M$ values of each PEP were determined in an assay mixture containing (SEQ ID NO:11) PQPQLPYPQPQLP as well as Suc-Ala-Pro-pNA as a competing substrate. The rates of disappearance of both substrates were determined by independent detection methods. The initial rate of disappearance of (SEQ ID NO:11) PQPQLPYPQPQLP was measured by HPLC, whereas the rate of consumption of Suc-Ala-Pro-pNA was measured spectrophotometrically. Both FM and MX PEP had a 5-fold higher specificity for the gluten peptide as compared to the chromogenic substrate, whereas the SC PEP showed a 7-fold increase in specificity for the gluten peptide (Table 2). This increase in specificity suggests that longer peptides may provide additional anchors at the catalytic site, a hypothesis that is consistent with the observation that Ala-Pro-pNA (which lacks an N-terminal succinyl group or a carboxybenzyl group) did not react with any of the PEPs.

To analyze the regiospecificity of hydrolysis of (SEQ ID NO:11) PQPQLPYPQPQLP by individual PEPs, samples corresponding to early time points were further analyzed by LC/MS/MS. The results, shown in FIG. 3A-3D, reveal that each PEP has unique subsite preferences. While the preferred site of cleavage by FM PEP was at the (SEQ ID NO:11) PQPQLPPYPIQPQLP position, MX PEP preferentially cleaved the same peptide at the (SEQ ID NO:11) PQPQLP|YPQPQLP position. SC had comparable preference for either site of cleavage. All enzymes preferentially cleaved the peptide at a proline located near the middle of the sequence, highlighting their functional difference from prolyl-specific exopeptidases such as DPP IV.

Chain Length Tolerance and Selectivity. It has been suggested that prolyl endopeptidases from the serine protease family are limited with regard to chain lengths of potential substrates. To test this hypothesis in the context of the three bacterial PEPs studied here, we compared their hydrolytic activities against a physiologically relevant 33-mer peptide sequence from wheat gliadin, (SEQ ID NO:12) LQLQPF-PQPQLPYPQPQLPYPQPQLP YPQPQPF (FIG. 4A). The FM PEP (0.1 µM) was able to hydrolyze 10 µM of the 33-mer in about 2-3 minutes, whereas the SC PEP required >1 hr to reach a comparable endpoint. Based on initial rates, the FM PEP was estimated to act 5-fold faster on the 33-mer than the MX PEP, and >20 fold faster than the SC PEP. Thus, the SC PEP appears to have a severe chain length restriction for long peptide substrates.

The intermediates and products from hydrolysis of the 33-mer by the FM and MX PEPs were analyzed by LC/MS/MS (FIG. 4B-C). Several features are noteworthy. First, even at relatively early time-points, the digestive products of the MX PEP were predominantly small fragments, whereas FM PEP digestion yielded a significant pool of long intermediates such as (fragment of SEQ ID NO:12) LQLQPF-PQPQLPYPQPQLP, (fragment of SEQ ID NO:12) LQLQPFPQPQLPYP and (fragment of SEQ ID NO:12) LQLQPFPQPQLP. Thus, although both PEPs are able to effectively proteolyze the 33-mer, they have distinct hydrolytic patterns on this complex substrate. In particular, either the MX PEP appears to be processive (i.e. for each 33-mer substrate molecule, it sequentially cleaves all the preferred sites in the chain prior to release), or alternatively the enzyme has a strong bias toward shorter chain substrates. It could also be noted that the C-terminal fragments generated by the two enzymes are different ((fragment of SEQ ID NO: 12) QPQPF for the FM PEP, and (fragment of SEQ ID NO: 12) YPQPQPF for the MX PEP). This finding is consistent with observed sub-site preference in the case of (SEQ ID NO: 11) PQPQLPYPQPQLP digestion.

To directly investigate chain length selectivity of the three enzymes, we co-incubated (SEQ ID NO: 11) PQPQLPYPQPQLP and (SEQ ID NO: 12) LQLQPF-PQPQLPYPQPQLPYPQPQLPYPQPQPF with each PEP (FIG. 6A-C) Both the SC PEP and the MX PEP showed a clear preference for the 13-mer peptide, whereas the FM PEP showed comparable selectivity for both peptides.

To further evaluate the substrate preferences, (SEQ ID NO:11) PQPQPLPYPQPQLP and the 33-mer were mixed with pepsin-treated gluten, and allowed to react with pancreatic enzymes in the presence of BBM and either FM PEP or MX PEP. As seen in the HPLC traces (FIG. 6A-B), the 33-mer had the longest retention time, whereas (SEQ ID NO:11) PQPQLPYPQPQLP and other medium-length gluten peptides eluted earlier. Here too the FM PEP proteolyzed (SEQ ID NO:11) PQPQLPYPQPQLP, the 33-mer and other gluten peptides at comparable rates (FIG. 6A). In the MX PEP digestion, (SEQ ID NO:11) PQPQLPYPQPQLP and other smaller peptides were rapidly broken down (in 10 minutes), whereas hydrolysis of the 33-mer occurred at a slower rate (FIG. 6B).

In Vivo Hydrolysis. To validate the implications of the above biochemical observations for peptide digestion in the intact small intestine, each PEP was co-perfused in the rat jejunum with the 33-mer peptide substrate, and the effluent collected at a distance of 15-20 cm from the point of perfusion was analyzed. In this live animal model, the impact of concerted action of the perfused (luminal) PEP and the brush border (surface) peptidases is assessed. As shown by the in vitro results above, while the BBM enzymes were insufficient to process the 33-mer, FM PEP promoted more complete breakdown of the 33-mer than both the MX and the SC PEP (FIG. 7). Within a PEP dose range of 50-500 µU/µl, the extent of 33-mer hydrolysis increased with increasing PEP dose, demonstrating that higher doses of PEP could accelerate gluten breakdown in the mammalian gut.

In light of recent findings that related the strong antigenicity of gliadin peptides to their exceptional digestive resistance, prolyl endopeptidases were identified as a potentially interesting family of enzymes for oral Celiac Sprue therapy. Understanding the enzymological properties of these enzymes is an essential prerequisite for such use. In the above study, prolyl endopeptidases from three bacterial sources were selected and expressed in *E. coli* as recombinant proteins, and were subsequently purified and characterized. Two of these enzymes (from *F. meningosepticum* and *S. capsulata*) have been reported earlier, whereas the third enzyme (from *M. xanthus*) represents a new member of the prolyl endopeptidase family.

In order to examine the endoproteolytic properties of these enzymes, it is important to utilize peptide substrates with internal cleavage sites. Although model substrates such as Z-Gly-Pro-pNA or Suc-Ala-Pro-pNA have been frequently used to identify and characterize polyl endopeptidases, these substrates alone do not provide adequate insight to differentiate endopeptidases from each other or from proline-specific aminopeptidases (such as dipeptidyl peptidase IV (DPP IV)). In the context of Celiac Sprue, two peptides ((SEQ ID NO:11) PQPQLPYPQPQLP and (SEQ ID NO:12) LQLQPF-PQPQLPYPQPQLPYPQPQLPYPQPQPF) have been recognized as useful probes for studying the fundamental properties of prolyl endopeptidases, as well as for their potential for detoxifying gluten. The peptide (SEQ ID NO:11) PQPQLPYPQPQLP contains an epitope found in γ-gliadins that has been shown to play an immunodominant role in the T cell mediated response to gluten in the Celiac gut. It cannot be cleaved by any gastric or pancreatic proteases and is also highly resistant to digestion by intestinal brush border membrane (BBM) peptidases, with only dipeptidyl carboxypeptidase I able to act upon it at a very limited rate. Thus, the efficiency of intestinal metabolism of this peptide can be expected to improve in the presence of an exogenous prolyl endopeptidase, as has been verified in this study. Treatment of this peptide with PEP results in cleavage at an internal proline residue, which in turn generates a new recognition site for brush border aminopeptidases. Thus, (SEQ ID NO:11) PQPQLPYPQPQLP represents a good probe for PEP specificity.

The 33-mer gliadin peptide (SE ID NO:12) LQLQPF-PQPQLPYPQPQLPYPQPQLPYPQPQPF was selected as a complementary probe for these studies, because it is a stable, physiologically derived product of gastric and pancreatic digestion of γ-gliadin, and strongly stimulates proliferation of gluten-reactive T cells from virtually all Celiac Sprue patients tested thus far. Therefore, endoproteolytic breakdown of this 33-mer peptide represents an especially challenging goal for an exogenous PEP. Like most other antigenic gluten peptides, the 33-mer contains multiple proline residues, and can be expected to present more than one cleavage site to a PEP. At the same time its multivalent character suggests that PEP action alone is unlikely to eliminate all residual antigenicity of this peptide. Consequently, combined action of a PEP and the endogenous peptidases of the intestinal brush border membrane is required for immunological neutralization and dietary assimilation of this long proline-rich peptide.

Figure 3:
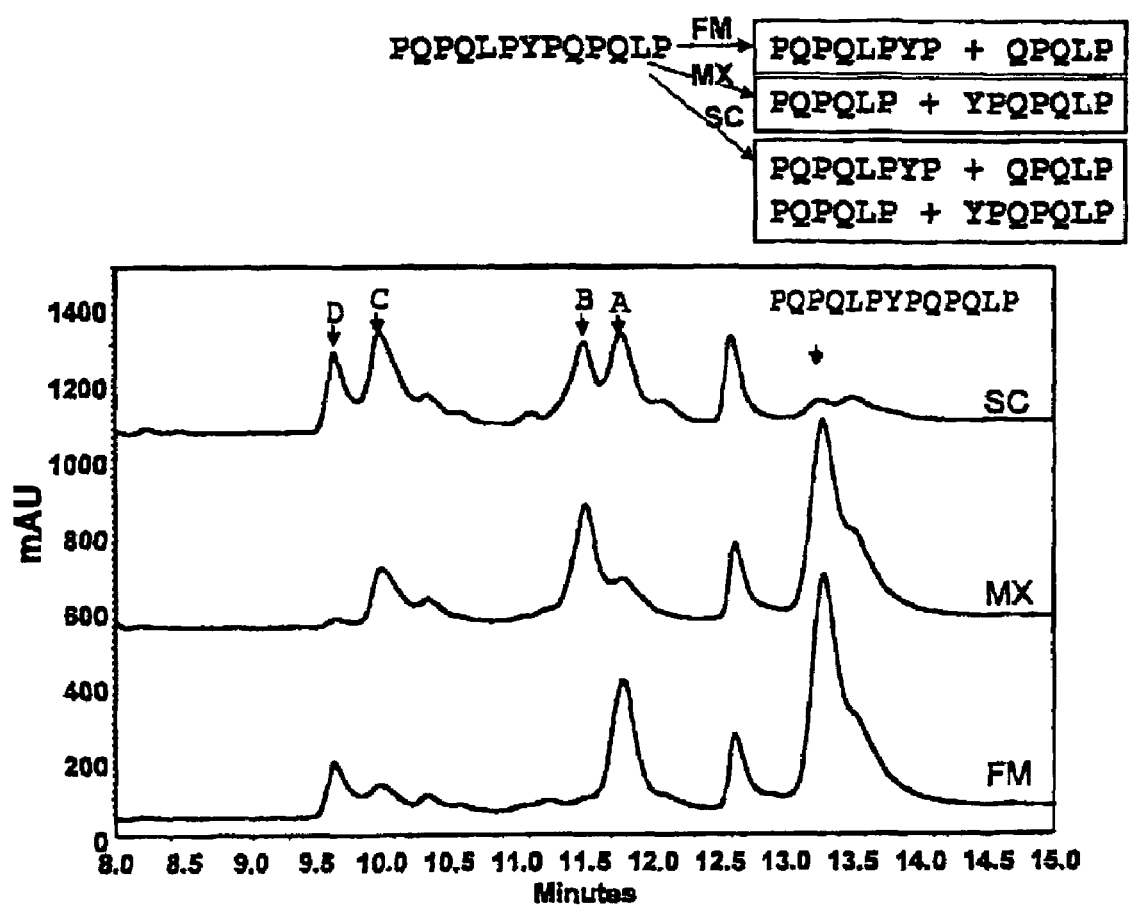
FIG. 3. Site specificity of PQPQLPYPQPQLP hydrolysis by individual PEPs. HPLC-UV (215 nm) traces are shown for each reaction mixture. Initial cleavage fragments (100 μM (SEQ ID NO:11) PQPQLPYPQPQLP, 0.1 μM enzyme, t=5 min) were identified by tandem mass spectrometry. The starting material (SEQ ID NO:11) PQPQLPYPQPQLP and the cleavage fragments A: (SEQ ID NO:11, aa. 1-8) PQPQLPYP, B: (SEQ ID NO:11, aa 7-13) YPQPQLP, C: (SEQ ID NO:12, aa 1-6) PQPQLP, D: (SEQ ID NO:11, aa 2-6) QPQLP) are indicated in the traces.

Our investigations into the molecular recognition features of three bacterial PEPs for two gliadin peptides have revealed at least two interesting and potentially important characteristics of these enzymes. First, although all three PEPs tested here exhibited high specific activity against reference chromogenic substrates (Table 1), they showed remarkable differences in chain length specificity (FIG. 3A-C). Whereas SC PEP and MX PEP had higher specificity for (SEQ ID NO:11) PQPQLPYPQPQLP than FM PEP (Table 2), the reverse was true for the longer 33-mer gliadin peptide (FIG. 4A), especially in the case of the SC PEP, which had extremely poor activity against the 33-mer.

Structural and biochemical analysis led to the proposal that the activity of PEPs is limited to substrates containing fewer than 30 amino acid residues. In that light the good activity of MX PEP and especially FM PEP against the 33-mer peptide is surprising. The broad chain length tolerance of FM PEP is vividly demonstrated in competitive in vitro and in vivo assays, where FM PEP was able to process longer and shorter substrates at comparable rates. Second, sequence analysis of the major proteolytic products derived from both gliadin substrates demonstrated that the PEP's had distinct sub-site specificity as well as regiospecificity in the context of the longer repetitive sequence. For example, the FM PEP preferentially cleaved at (SEQ ID NO:11) PQPQLPYPIQPQLP, whereas the MX PEP preferred the SEQ ID NO:11 PQPQLP|YPQPQLP site, and the SC PEP had comparable activity toward either site.

Similarly, sequence analysis of initial hydrolytic products of the 33-mer peptide underscored regiochemical differences between FM PEP and MX PEP. Whereas MX PEP treatment generated fragments mostly of 4-5 residues (presumably processed sequentially from both termini), FM PEP yielded longer intermediates (presumably as a result of a preferential cleavage near the center of the peptide). Thus, the active sites of these enzymes are clearly different, which in turn has potential implications for the use of these enzymes detoxifying dietary gluten for a Celiac Sprue patient.

In addition to analyzing substrate specificity, we have also investigated other therapeutically relevant properties of our set of three PEPs. They include pH dependence of enzyme activity, acid tolerance of the protein, and resistance toward inactivation by gastric, pancreatic and intestinal proteases/peptidases. All enzymes have a pH activity profile that is well matched to the mildly acidic environment of the upper small intestine (pH 6-6.5). They also appear to be moderately stable toward acid exposure as well as pancreatic protease (but not pepsin) action, with the MX PEP being the most stable. The enzymes also retain activity in the intact small intestinal lumen of a rat, indicative of their stability toward both intestinal secretions as well as brush border membrane peptidases. Finally, the expression levels of these enzymes vary significantly in recombinant $E.$ $coli.$ Specifically, in comparison to the FM PEP, the expression levels of SC and MX PEPs were substantially superior.

The porcine brain PEP has a didomain architecture, including an unusual β-propeller domain that appears to regulate proteolysis. Pairwise sequence alignments between this structurally characterized PEP and FM, MX and SC PEP reveal 39% (49%), 36% (45%) and 40% (48%) identity (similarity), respectively. These alignments also suggest that the bacterial PEPs are comprised of a catalytic and a β-propeller domain. Since their active sites are predicted to lie near the interface between the two domains, mutagenesis at the inter-domain interface could alter protein dynamics and in turn affect substrate tolerance and specificity.

The above results provide a basis for protein engineering efforts of PEP enzymes. This family of serine proteases includes numerous other putative homologs whose cDNAs have been sequenced but whose gene products remain to be characterized. In light of the favorable properties of the MX PEP, which was expressed and characterized for the first time as part of this study, it will be useful to screen additional wild-type enzymes.

Example 2

Heterologous Expression of PEP in *Lactobacilli*

In one embodiment of the present invention, a Celiac Sprue patient is provided with a recombinant organism modified to express a PEP of the invention. The recombinant organism is selected from those organisms that can colonize the intestinal mucosa without detriment to the patient, thereby providing an endogenous source of PEP to the patient. As one example, *Lactobacilli* such as *L. casei* and *L. plantarium* can colonize the intestinal mucosa and secrete PEP enzymes locally. Given their widespread use in food processing, they can also be used as an efficient source of PEP for industrial (to treat foodstuffs) and medical (to prepare PEP for pharmaceutical formulation) use. PEPs are expressed in such *lactobacilli* using standard recombinant DNA technologies. For example, Shaw et al. (Shaw, D M, Gaerthe, B; Leer, R J, Van der Stap, J G M M, Smittenaar, C.; Den Bak-Glashouwer, Heijne, M J, Thole, J E R, Tielen F J, Pouwels, P H, Havenith, C E G (2000) Immunology 100, 510-518) have engineered *Lactobacilli* species to express intracellular and surface-bound tetanus toxin. The intact PEP genes (including leader sequences for efficient bacterial secretion) are cloned into shuttle expression vectors such as pLP401 or pLP503 under control of the (regulatable) amylase promoter or (constitutive) lactate dehydrogenase promoter, respectively. Alternatively, recombinant food grade *Lactobacilli* strains are generated by site specific recombination technology (e.g. see. Martin M C, Alonso, J C, Suarez J E, and Alvarez M A Appl. Env. Microbiol. 66, 2599-2604, 2000). Standard cultivation conditions are used for *Lactobacilli* fermentation, such as those described by Martin et al.

Example 3

Heterologous Expression of PEP in Yeasts

Both naturally occurring and recombinant cells and organisms are used to produce the glutenases useful in practice of the present invention. Preferred glutenases and producing cells include those from organisms known to be Generally Regarded as Safe, such as *Flavobacterium, Aeromonas, Sphingomonas, Lactobacillus, Aspergillus, Xanthomonas, Pyrococcus, Bacillus* and *Streptomyces*. Extracellular glutenase enzymes may be obtained from microorganisms such as *Aspergillus oryzae* and *Lactobacillus casei*. Preferred cells include those that are already used in the preparation of foodstuffs but have been modified to express a glutenase useful in the practice of the present invention. As one example, yeast strains such as *Saccharomyces cerevisiae* are useful for high level expression of secreted heterologous proteins. Genes encoding any of the PEPs described above (mature protein only) are cloned in expression plasmids designed for optimal production of secreted proteins. An example of such a heterologous expression strategy is described in Parekh, R. N. and Wittrup, K. D. (Biotechnol. Prog. 13, 117-122, 1997). Either self-replicating (e.g. 2 micron) or integrating (e.g. pAUR101)

vectors can be used. The GAL1-10 promoter is an example of an inducible promoter, whereas the ADH2 promoter is an example of a constitutive promoter. The cDNA encoding the mature PEP is fused downstream of a leader sequence containing a synthetic pre-pro region that includes a signal cleavage site and a Kex2p cleavage site. *S. cerevisiae* BJ5464 can be used as a host for production of the peptidase. Shake-flask fermentation conditions are described by Parekh and Wittrup in the above-cited reference. Alternatively, high cell density fed-batch cultures can be used for large scale production of the peptidases; a representative procedure for this purpose is described in Calado, C. R. C, Mannesse, M., Egmond, M., Cabral, J. M. S. and Fonseca, L. P. (Biotechnol. Bioeng. 78, 692-698, 2002).

Example 4

Enteric Capsule Formulation of Prolyl Endopeptidase

Gelatin capsules are filled with 100 mg *Myxococcus xanthus* prolyl endopeptidase and 10 mg of silicon dioxide. The capsules are enterically coated with Eudragit polymer and put in a vacuum chamber for 72 hours. The capsules are then held at a range of temperature of 10° C. to 37° C. and a controlled humidity level of 35-40%.

Example 5

Studies of Enteric Capsule Formulation of Prolyl Endopeptidase

A study is conducted where patients with Celiac Sprue are enrolled in a two week-long study. Gelatin capsules containing 90% *Myxococcus xanthus* prolyl endopeptidase mixed with 10% silicon dioxide are used. The capsules are hand-filled with the mixture, banded, and coated with a 10% Sureteric enteric coating (a polymer of polyvinylacetatephthalate developed by the Canadian subsidiary of Merck & Company). Samples are acid-tested by exposing the coating to 1N HCL for one hour in order to simulate the acid environment of the stomach. The capsules are then put in a vacuum chamber for 72 hours.

Two 100 mg capsules are administered to each patient prior to each meal. The patients are instructed to eat all kinds of food without abstaining from those that were known to cause distress, e.g., bloating, diarrhea, and cramps.

Example 6

Enteric Pill Formulation of Prolyl Endopeptidase 400 mg of L-tartaric acid and 40 mg of polyethylene glycol-hydrogenated castor oil (HCO-60) are dissolved in 5 ml of methanol. This solution is placed in a mortar previously warmed to 30° C. To the solution is added 100 mg of *Myxococcus xanthus* prolyl endopeptidase. Immediately after the addition of PEP, the mixture is stirred with a pestle under a hot air current (40° C.) and then placed in a desiccator under vacuum overnight to remove the solvent. The resulting solid-mass is pulverized with a pestle and kneaded with 30 mg of sodium bicarbonate and a small amount of 70% ethanol. The mixture is then divided and shaped into pills of about 2 mm size and thoroughly dried. The dried pills are given a coating of hydroxypropylmethylcellulose phthalate (HP-55) to obtain an enteric formulation.

Example 7

Endoprotease Activity

The gene for an endoprotease (EPB2; PubMed accession number U19384, nt 94-1963) from barley (*Hordeum vulgare* subsp. *vulgare*) was subcloned into a pET28b (Invitrogen) vector using BamH1 and EcoR1 insertion sites; the resulting plasmid was designated pMTB1. An inactive 43 kDa proprotein form of EPB2 was expressed from pMTB1 in the cytoplasm of BL21 *E. coli* cells. The proprotein was solubilized from the inclusion bodies using 7 M urea. The solubilized protein was purified on a Ni-NTA column. Auto-activation of proEPB2 to its mature, active form was achieved by addition of citrate-phosphate buffer, pH 3 (prepared by mixing 0.1 M sodium citrate and 0.2 M sodium phosphate). Under such acidic conditions, proEPB2 converts rapidly into a mature form with a molecular weight of 30 kDa (FIG. 2). By 72 hours, mature EPB2 undergoes autolysis. N-terminal sequencing yielded an N-terminal sequence beginning with VSDLP.

Under acidic conditions, the mature form of EPB2 efficiently digests purified α2-gliadin, a source of peptides that are immunogenic to people who suffer from Celiac Sprue. The cysteine proteinase inhibitor, leupeptin, inhibits this activity, confirming its mechanism as a cysteine protease. The pH optimum of proEPB2 activation and a2-gliadin digestion is 2.4-3.5, which can therefore provide a treatment for Celiac Sprue consisting of oral administration of proEPB2.

Example 8

Formulation and Efficacy Analysis of *M. xanthus* PEP

Lyophilization of *M. xanthus* PEP was performed as follows. The PEP was purified as described in Example 1, and concentrated to an initial concentration of 7.7 mg/ml by Tangential-Flow Filtration (TFF) using a 10K MWCO Pellicon difiltration membrane (Millipore, PLCGC10, 50 cm, Cat. No. PXC010C50). TFF (using a LabScale TFF from Millipore, Cat. No. 29751) was performed for approximately 12 hours (pressure of 50 psi (retentate)/30 psi (permeant)), with periodic addition to the reservoir of 50 mM Sodium Phosphate, 3% Sucrose pH 7.5. Thereafter, PEG-4000 was added with a target concentration of 1%. The final protein concentration was 70-100 mg/ml. This material was centrifuged, then lyophilized. The lyophilization was performed in square petri dishes (Falcon Cat. No. 35-1112) in a DuraStop lyophilizer using parameters outlined in the Table below. Typically, 0.7-0.85 mg PEP was present per mg of lyophilized material. No loss of specific activity of the PEP was observed upon lyophilization.

| Step | Temperature | Pressure | Duration | Ramp Rate |
| --- | --- | --- | --- | --- |
| Freezing 1 | −50° C. | Atmospheric | 2 hrs | 0.3° C./minute |
| Annealing | −35° C. | Atmospheric | 3 hrs | 0.3° C./minute |
| Freezing 2 | −50° C. | Atmospheric | 2 hrs | 0.3° C./minute |
| 1° Drying | −20° C. | 100 mTorr | 16.9 hrs | 0.5° C./minute |
| 2° Drying | +25° C. | 100 mTorr | 8.0 hrs | 0.2° C./minute |

*P. Temp. = Avg. Product Temp. at end of step.
**1° = Primary Drying.
***2° = Secondary Drying Blending for the *M. xanthus* PEP was performed as follows. Lyophilized cakes were pulverized to a light powder. All samples were weighed for recovery and stored in sealed 50 mL conical vials at 4° C. A blend was prepared as shown below. The excipients were selected to provide proper flow and disintegration properties for the blended mixture.

| Order of Addition | Excipient | Percentage |
|---|---|---|
| 1 | Lyophilized enzyme cake/powder | 63% |
| 2 | Calcium Silicate | 2% |
| 3 | Talc | 5% |
| 4 | Crospovidone | 5% |
| 5 | Avicel | 25% |

The lyophilized enzyme and excipients were blended in a V-blender for several hours. The material was then used to make enteric-coated capsules or tablets. 100-150 mg *M. xanthus* PEP could be loaded into a single hard gelatin capsule, size 00 (Capsugel). Alternatively, Vcap vegetable capsules (size 00, Capsugel) can also be used with no impact on enzyme activity.

For enteric coating of the capsules, an enteric coating solution was prepared as shown below:

| Order of Addition | Excipient | Amount added |
|---|---|---|
| 1 | RODI water | 49.5 mL |
| 2 | Talc | 8.1 g |
| 3 | Eudragit L50 D-55 | 111.0 mL |
| 4 | Triethyl Citrate | 1.62 mL |

The enteric coating was mixed vigorously in a beaker on a stir plate. The solution was then decanted into a spray bottle. Rat capsules were carefully spread on paper towels in groups of 20 and the enteric coating solution sprayed onto the capsules. Warm air was used to partially dry the capsules before moving them to a dry paper towel where they air-dried for 30 minutes before the next coat was applied. A total of 3 coats were applied in order to cover all sides of the capsules. These were air dried several hours before being transferred to a storage container. Although some activity of the PEP is lost as a result of enteric coating, a substantial fraction of the activity is retained, and is stable for at least 1 month at 4 C storage.

An alternative method to formulate the enzyme for intestinal delivery is as an enteric-coated tablet. Tablets have the advantage of more rapid dissolution in the weakly acidic environment of the upper small intestine. Another advantage of the tablet formulation is that more enzyme can be compacted into a smaller volume than for a capsule. Their primary liability is that proteins frequently denature under high pressures. In a method of tablet preparation of *M. xanthus* PEP, the same lyophilized blend as above was used. Tablets were prepared at a punch strength of 3000 psi held for 15 seconds. No activity was lost in the process, demonstrating the feasibility of tablet formulations of this enzyme.

To test the efficacy of the enteric-coated oral capsule formulation described above, two types of tests were performed. In vitro dissolution tests were performed on a Hanson SR8-Plus Dissolution Tester using Simulated Gastric Fluid (SGF; 2 g/L NaCl, pH 1.2, adjusted using 6 N HCl) and Simulated Intestinal Fluid (SIF; 6 g/L monobasic potassium phosphate with or without 10 g/L pancreatin, pH 6.8, adjusted using 5 N NaOH). Enteric coated capsules were first tested for resistance to dissolution in SGF for up to 2 h at 37° C. No protein release was noted. Subsequently the capsules were subjected to similar dissolution tests in SIF at 37° C. A substantial fraction of the encapsulated material was released in 15 min. By 30 min the material had been completely released.

In vivo tests of the capsules were performed in rats using smaller hard gelatin capsules (Size 9 capsules, Torpac). Approximately 16 mg of the lyophilized formulation blend was encapsulated in each enteric-coated capsule, corresponding to ~7 mg PEP. Rats fasted overnight were administered via oral gavage one PEP or placebo capsule along with a measured quantity (300 mg gluten/kg body weight) of gluten syrup prepared as follows. 300 g commercially available wheat gluten flour (Bob's Red Mill, Milwaukie Oreg.) was added to 10 L of a 0.01 M HCl solution to achieve a pH of 2.0. Pepsin (6.0 g, American Laboratories) was added. After incubation at 37° C. for 1 h, the pH was adjusted to 2.0 by addition of 35 ml 1M HCl. After maintenance for an additional 2 h at 37° C., the solution was neutralized by addition of 35 g of $Na_2HPO_4$, and the pH was adjusted to 7.9 with 10 M NaOH (32.5 ml). Trypsin/Chymotrypsin powder (3.75 g) (Enzyme Development Corp; 1000 USP/mg in trypsin, 1000 USP/mg in chymotrypsin) was then added, the reaction maintained at 37° C. for 2 hours, pH 7.9 (pH re-adjustment to 7.9 after 1 hour, with 10 M NaOH) and heated at 100° C. for 15 minutes to inactivate the enzymes. The final gluten solution was filtered through cheesecloth to remove residual large particles. One PEP capsule-fed animal and one sham capsule-fed animal was sacrificed after 45 min and 90 min each, and the small intestinal contents were analyzed for gluten content via C18 reversed phase HPLC. Chromatograms were normalized for total protein content in each sample. Top=45 min, Bottom=90 min (green=placebo, blue=PEP capsule).

Gluten-derived peptides elute in the 20-30 min region. At 45 min as well as 90 min, the pepsin-trypsin-chymotrypsin treated gluten was minimally metabolized in the sham-fed animals, whereas it appears to be extensively metabolized. Together, these results indicate that enteric-coated PEP capsules can survive the gastric environment of the stomach, and catalyze proteolysis of dietary peptides in the small intestine.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

The invention claimed is:

1. A formulation comprising:
a combination of a prolyl endopeptidase (PEP) and *Hordeum vulgare* cysteine endoprotease B in an amount effective to decrease toxic gluten oligopeptide levels in a foodstuff and a pharmaceutically acceptable excipient, wherein said prolyl endopeptidase has a Kcat/Km of at least 250 $s^{-1}$ $M^{-1}$ for cleaving (SEQ ID NO:11) PQPQLPYPQPQLP.

2. The formulation according to claim 1, wherein said prolyl endopeptidase is *Flavobacterium meningosepticum* PEP, *Myxococcus xanthus* PEP, *Sphingomonas capsulata* PEP, or *Penicillium citrinum* PEP.

3. A combination of a prolyl endopeptidase (PEP) and *Hordeum vulqare* cysteine endoprotease B in an amount effective to decrease toxic gluten oligopeptide levels in a foodstuff and a pharmaceutically acceptable excipient, wherein said prolyl endopeptidase is *Sphingomonas capsulata* PEP.

4. The formulation according to claim 1, wherein said formulation is suitable for oral administration.

5. The formulation according to claim 1, wherein said formulation comprises an enteric coating.

6. The formulation of claim 1, wherein the cysteine endoprotease B is recombinantly produced.

7. The formulation of claim 6, wherein the cysteine endoprotease is produced in *E. coli*.

8. The formulation of claim 1, wherein the cysteine endoprotease B is in a proenzyme form that is activated under acidic conditions.

9. The formulation of claim 1, wherein the cysteine endoprotease B is purified by affinity chromatography.

10. The formulation of claim 1, wherein the cysteine endoprotease B comprises a histidine tag.

11. The formulation according to claim 6, wherein the cysteine proteinase B is lyophilized.

12. The formulation according to claim 1, wherein the mixture of a prolyl endopeptidase and cysteine endoprotease B is formulated in a pharmacologic unit dose.

13. The combination of claim 3, wherein the *Sphingomonas capsulata* PEP is recombinantly produced.

14. The formulation of claim 6, wherein the *Sphingomonas capsulata* PEP is produced in *E. coli*.

15. The combination of claim 3, wherein the *Sphingomonas capsulata* PEP is purified by affinity chromatography.

16. The combination of claim 15, wherein the *Sphingomonas capsulata* PEP comprises a histidine tag.

17. The combination of claim 3, wherein the *Sphingomonas capsulata* PEP has been lyophilized.

* * * * *